(12) United States Patent
Felföldi et al.

(10) Patent No.: US 9,458,207 B2
(45) Date of Patent: Oct. 4, 2016

(54) METHODS FOR REFOLDING G-CSF FROM INCLUSION BODIES

(71) Applicant: Richter Gedeon Nyrt., Budapest (HU)

(72) Inventors: Ferenc Felföldi, Budapest (HU);
Andras Ballagi, Budapest (HU); János Bécsi, Budapest (HU)

(73) Assignee: Richter Gedeon Nyrt., Budapest (HU)

(*) Notice: Subject to any disclaimer, the term of this patent is extended or adjusted under 35 U.S.C. 154(b) by 0 days.

(21) Appl. No.: 14/386,128

(22) PCT Filed: Mar. 18, 2013

(86) PCT No.: PCT/EP2013/055531
§ 371 (c)(1),
(2) Date: Sep. 18, 2014

(87) PCT Pub. No.: WO2013/068603
PCT Pub. Date: May 16, 2013

(65) Prior Publication Data
US 2015/0057439 A1 Feb. 26, 2015

(30) Foreign Application Priority Data

Mar. 19, 2012 (HU) .................................... 1200172

(51) Int. Cl.
*C07K 14/535* (2006.01)
*C07K 14/245* (2006.01)

(52) U.S. Cl.
CPC .......... *C07K 14/245* (2013.01); *C07K 14/535* (2013.01)

(58) Field of Classification Search
None
See application file for complete search history.

(56) References Cited

U.S. PATENT DOCUMENTS

| | | | |
|---|---|---|---|
| 5,055,555 A | 10/1991 | Sassenfeld | |
| 5,681,720 A | 10/1997 | Kuga et al. | |
| 5,849,883 A | 12/1998 | Boone et al. | |
| 5,919,757 A * | 7/1999 | Michaelis et al. | 424/85.1 |
| 6,489,450 B2 | 12/2002 | Randolph et al. | |
| 6,606,183 B2 * | 8/2003 | Ikai et al. | 359/265 |
| 8,148,500 B2 * | 4/2012 | Cox et al. | 530/399 |
| 8,617,531 B2 * | 12/2013 | Cox et al. | 424/85.5 |
| 8,703,123 B2 * | 4/2014 | Hinderer et al. | 424/124 |
| 2002/0150979 A1 * | 10/2002 | Naitou et al. | 435/69.1 |
| 2005/0058621 A1 * | 3/2005 | Cox, III | 424/85.1 |
| 2005/0159589 A1 * | 7/2005 | Gaberc Porekar et al. | 530/351 |
| 2005/0283000 A1 * | 12/2005 | Menart et al. | 530/351 |
| 2008/0171857 A1 * | 7/2008 | Komath et al. | 530/416 |
| 2008/0260684 A1 * | 10/2008 | Dietrich | C07K 14/535 424/85.1 |
| 2012/0093765 A1 * | 4/2012 | Somani et al. | 424/85.1 |
| 2015/0044721 A1 | 2/2015 | Felföldi et al. | |

FOREIGN PATENT DOCUMENTS

| | | | |
|---|---|---|---|
| EP | 0 219 874 A2 | 4/1987 | |
| EP | 1 630 173 A2 | 3/2006 | |
| EP | 1 837 346 A2 | 9/2007 | |
| EP | 2341061 * | 7/2011 | C07K 1/00 |
| WO | WO 87/01132 A1 | 2/1987 | |
| WO | WO/89/10932 * | 11/1989 | C07K 3/28 |
| WO | WO 98/53072 A1 | 11/1998 | |
| WO | WO 00/02901 A1 | 1/2000 | |
| WO | WO 01/04154 A1 | 1/2001 | |
| WO | WO 01/87925 A2 | 11/2001 | |
| WO | WO 03/051922 A1 | 6/2003 | |
| WO | WO 04/001056 A1 | 12/2003 | |
| WO | WO 2006/097944 A2 | 9/2006 | |
| WO | WO 2006/135176 A1 | 12/2006 | |
| WO | WO 2008/096370 A2 | 8/2008 | |
| WO | WO2008096370 * | 8/2008 | C12N 15/09 |
| WO | WO 2010/146599 A1 | 12/2010 | |

OTHER PUBLICATIONS

Singh et al. Isolation, Solubilization, Refolding, and Chromatographic Purification of Human Growth Hormone from Inclusion Bodies of *Escherichia coli* Cells. Methods in Molecular Biology, vol. 308: Therapeutic Proteins: Methods and Protocols, pp. 163-176, 2005, Edited by: C. M. Smales and D. C. James © Humana Press Inc., Totowa, NJ.*
Dasari et al. Optimization of the downstream process for high recovery of rhG-CSF from inclusion bodies expressed in *Escherichia coli*. Process Biochemistry. 43, 566-575, 2008.*
Schwanke et al. Molecular cloning, expression in *Escherichia coli* and production of bioactive homogeneous recombinant human granulocyte and macrophage colony stimulating factor, Int. J. Biological Macromolec. 45, 97-102, 2009.*
Ricci et al. pH Dependence of structural stability of interleukin-2 and granulocyte colony-stimulating factor, Protein Science, 12, 1030-1038, 2003.*
Nordborg et al. Recent advances in polymer monoliths for ionexchange chromatography, Anal. Bioanal. Chem. 394, 71-84, 2009.*
Supelco. Catalog of Chromatography products, pp. 58-59, 2007-2008.*
Kelly et al., Low-conductivity buffers for high-sensitivity NMR measurements. J.Am.Chem.Soc., 124, 12013-12019, 2002.*
[No Author Listed], Filgrastim concentrated solution. European Pharmacopoeia. 7th ed. Jul. 15, 2011; Strasbourg: Council of Europe: 2015-18.

(Continued)

*Primary Examiner* — Elly-Gerald Stoica
(74) *Attorney, Agent, or Firm* — Wolf, Greenfield & Sacks, P.C.

(57) ABSTRACT

New methods for the refolding of recombinant granulocyte colony stimulating factor (G-CSF) from inclusion bodies are disclosed. The methods comprise two refolding steps. In particular, the methods comprise the solubilizing of G-CSF with a solubilizing agent, the oxidative refolding (first refolding step) of G-CSF in the presence of the solubilizing agent and an oxidizing agent, the efficient removal of the solubilizing agent, and a second refolding step to complete the folding of G-CSF in the absence of the solubilizing agent. Various methods are described for the efficient removal of the solubilizing agent from partially refolded G-CSF.

19 Claims, 4 Drawing Sheets

(56) References Cited

OTHER PUBLICATIONS

Barut et al., Methacrylate-based short monolithic columns: enabling tools for rapid and efficient analyses of biomolecules and nanoparticles. J Sep Sci. Jun. 2008;31(11):1867-80. doi:10.1002/jssc.200800189.

Burgess, Purification of overproduced *Escherichia coli* RNA polymerase sigma factors by solubilizing inclusion bodies and refolding from Sarkosyl. Methods Enzymol. 1996;273:145-9.

Dale, Colony-stimulating factors for the management of neutropenia in cancer patients. Drugs. 2002;62 Suppl 1:1-15.

Devlin et al., Alteration of amino-terminal codons of human granulocyte-colony-stimulating factor increases expression levels and allows efficient processing by methionine aminopeptidase in *Escherichia coli*. Gene. May 15, 1988;65(1):13-22.

Dietrich et al., Industrial Protein Folding. Proteomics. BIOforum Europe. Darmstadt, Germany; Jan. 2003; 34-36.

Heidari et al., Expression, purification, and in vitro biological activities of recombinant bovine granulocyte-colony stimulating factor. Vet Immunol Immunopathol. Aug. 30, 2001;81(1-2):45-57.

Holloway, Applications of recombinant DNA technology in the production of glycosylated recombinant human granulocyte colony stimulating factor. Eur J Cancer. 1994;30A Suppl 3:S2-6.

Kang et al., High level expression and simple purification of recombinant human granulocyte colony-stimulating factor in *E. coli*. Biotechnology Letters. Jul. 1995;17(7):687-92.

Khalilzadeh et al., Process development for production of human granulocyte-colony stimulating factor by high cell density cultivation of recombinant *Escherichia coli*. J Ind Microbiol Biotechnol. Dec. 2008;35(12):1643-50. doi: 10.1007/s10295-008-0408-8. Epub Aug. 6, 2008.

Lu et al., Folding and oxidation of recombinant human granulocyte colony stimulating factor produced in *Escherichia coli*. Characterization of the disulfide-reduced intermediates and cysteine—serine analogs. J Biol Chem. May 5, 1992;267(13):8770-7.

Marston, The purification of eukaryotic polypeptides synthesized in *Escherichia coli*. Biochem J. Nov. 15, 1986;240(1):1-12.

Molineux, The design and development of pegfilgrastim (PEG-rmetHuG-CSF, Neulasta). Curr Pharm Des. 2004;10(11):1235-44.

Ostervala, Purification and renaturation of recombinant proteins produced in *Escherichia coli* as inclusion bodies. GE Healthcare. Application note 18-1112-33 AC. Apr. 2007:4 pages.

Rao et al., A purification method for improving the process yield and quality of recombinant human granulocyte colony-stimulating factor expressed in *Escherichia coli* and its characterization. Biotechnol Appl Biochem. Jun. 2008;50(Pt 2):77-87.

Rudolph et al., In Vitro folding of inclusion body proteins. FASEB J. Jan. 1996;10(1):49-56.

Vanz et al., Human granulocyte colony stimulating factor (hG-CSF): cloning, overexpression, purification and characterization. Microb Cell Fact. Apr. 4, 2008;7:13. doi:10.1186/1475-2859-7-13.

Wang et al., Refolding with simultaneous purification of recombinant human granulocyte colony-stimulating factor from *Escherichia coli* using strong anion exchange chromatography. Chinese Chemical Letters. 2005;16(3):389-92.

Welte et al., Filgrastim (r-metHuG-CSF): the first 10 years. Blood. Sep. 15, 1996;88(6):1907-29.

Wingfield et al., Characterization of recombinant-derived granulocyte-colony stimulating factor (G-CSF). Biochem J. Nov. 15, 1988;256(1):213-8.

Zsebo et al., Recombinant human granulocyte colony stimulating factor: molecular and biological characterization. Immunobiology. Sep. 1986;172(3-5):175-84.

\* cited by examiner

Figure 1: Two-step refolding strategy for production of biologically active G-CSF
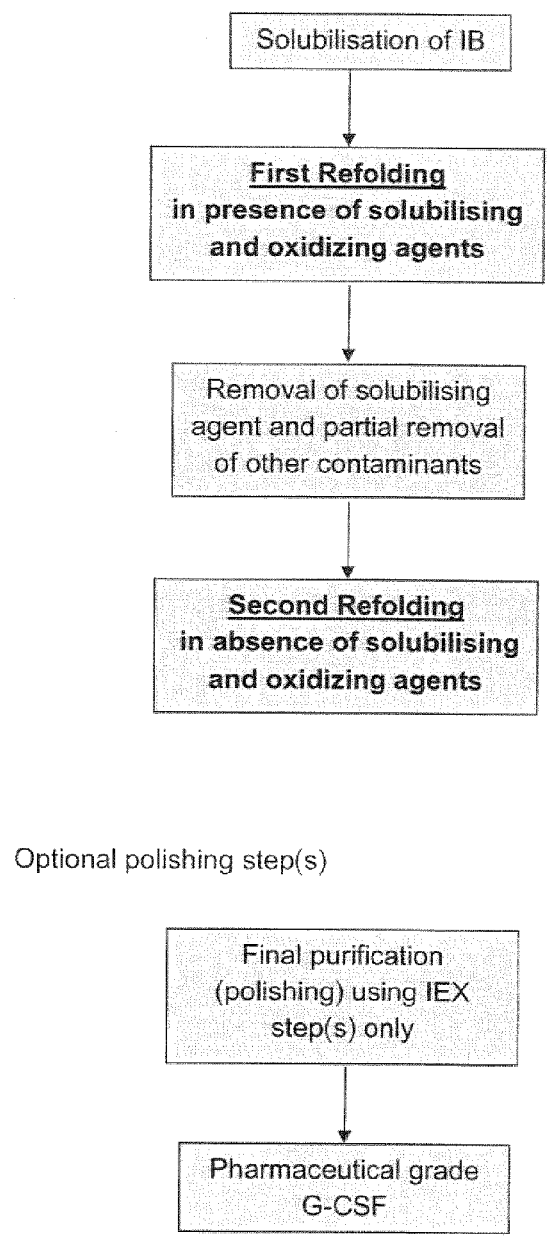

Figure 2: Example of a Refolding and purification scheme for G-CSF from inclusion bodies (IB) according to the invention
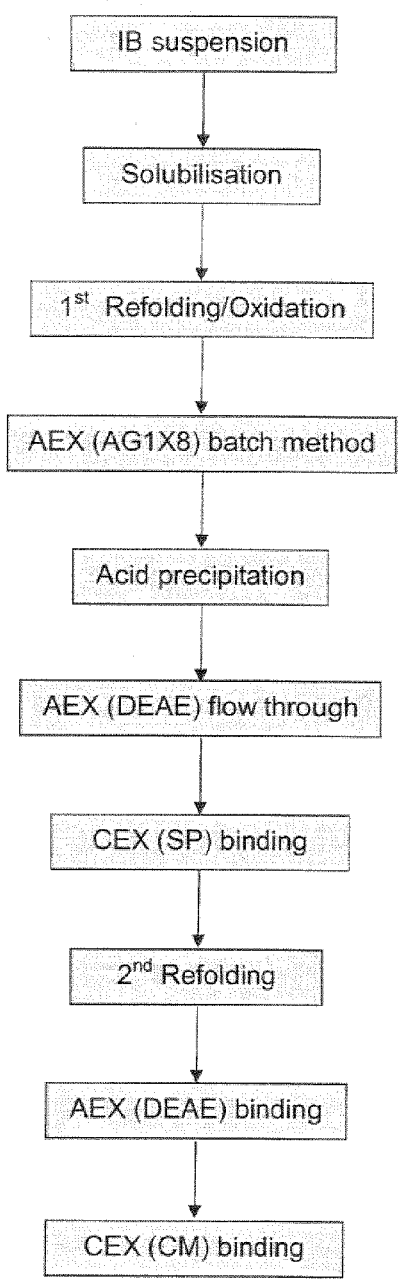

SEQUENCE LISTING

```
<160> NUMBER OF SEQ ID NOS: 3

<210> SEQ ID NO 1
<211> LENGTH: 174
<212> TYPE: PRT
<213> ORGANISM: Homo sapiens
```

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 174
<212> TYPE: PRT
<213> ORGANISM: Bos taurus

<400> SEQUENCE: 2

Thr Pro Leu Gly Pro Ala Arg Ser Leu Pro Gln Ser Phe Leu Leu Lys
1               5                   10                  15

Cys Leu Glu Gln Val Arg Lys Ile Gln Ala Asp Gly Ala Glu Leu Gln
            20                  25                  30

Glu Arg Leu Cys Ala Ala His Lys Leu Cys His Pro Glu Glu Leu Met
        35                  40                  45

Leu Leu Arg His Ser Leu Gly Ile Pro Gln Ala Pro Leu Ser Ser Cys
    50                  55                  60

Ser Ser Gln Ser Leu Gln Leu Arg Gly Cys Leu Asn Gln Leu His Gly
65                  70                  75                  80

Gly Leu Phe Leu Tyr Gln Gly Leu Leu Gln Ala Leu Ala Gly Ile Ser
                85                  90                  95

Pro Glu Leu Ala Pro Thr Leu Asp Thr Leu Gln Leu Asp Val Thr Asp
            100                 105                 110

Phe Ala Thr Asn Ile Trp Leu Gln Met Glu Asp Leu Gly Ala Ala Pro
        115                 120                 125

Ala Val Gln Pro Thr Gln Gly Ala Met Pro Thr Phe Thr Ser Ala Phe
    130                 135                 140

Gln Arg Arg Ala Gly Gly Val Leu Val Ala Ser Gln Leu His Arg Phe
145                 150                 155                 160

Leu Glu Leu Ala Tyr Arg Gly Leu Arg Tyr Leu Ala Glu Pro
                165                 170

<210> SEQ ID NO 3
<211> LENGTH: 175

```
<212> TYPE: PRT
<213> ORGANISM: Homo sapiens

<400> SEQUENCE: 3

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

METHODS FOR REFOLDING G-CSF FROM INCLUSION BODIES

RELATED APPLICATION

This application is a national stage filing under 35 U.S.C. §371 of international application PCT/EP2013/055531, filed Mar. 18, 2013, which was published under PCT Article 21(2) in English, the disclosures of which is incorporated by reference herein in its entirety.

FIELD OF THE INVENTION

The present invention relates to new methods for refolding G-CSF (colony stimulating factor) from inclusion bodies. In particular, it relates to a method comprising two refolding steps. The invention relates to a method for refolding G-CSF by (a) solubilising G-CSF, (b) oxidative refolding (first refolding step, in the presence of solubilising agent), (c) removing the solubilising agent and (d) a second refolding step (in the absence of solubulising agent). Also, the present invention relates to new methods for removing the solubilising agent.

BACKGROUND OF THE INVENTION

The endogenous hematopoetic growth factor, granulocyte-colony stimulating factor (G-CSF, synonym "colony-stimulating factor 3"=CSF3) regulates the proliferation and differentiation of progenitor cells within the bone marrow and the release of mature neutrophilic granulocytes ("neutrophils") into the peripheral blood. Cancer chemotherapy, which affects rapidly dividing cells, frequently leads to a side effect termed "neutropenia". Neutropenia is a decrease in counts of neutrophils in the peripheral blood and affects more than one of three patients receiving myelosuppressive chemotherapy for cancer. Patients driven into neutropenia can develop fever ("febrile neutropenia") and have an increased risk for infections. Life-threatening gastrointestinal and pulmonary infections occur, as does sepsis. A subsequent cycle of chemotherapy may have to be delayed until the patient has recovered from neutropenia. Recombinant human G-CSF is an effective pharmaceutical substance and successfully applied to treat chemotherapy-induced neutropenia. It restores the number of neutrophils in the blood and keeps it above the critical level (Dale 2002).

Natural human G-CSF is an O-glycosylated protein consisting of 174 amino acids and is relatively hydrophobic. The carbohydrate chain in the glycosylated form is located at threonine 133. Besides this major form another splice form can occur in vivo which bears additional three amino acids (Zsebo 1986). When recombinant human G-CSF is expressed in *E. coli*, the following can be observed: First, the recombinant protein is produced in inclusion bodies; second, the resulting G-CSF molecule is devoid of the natural carbohydrate chain, and third, the recombinant G-CSF bears an additional, N-terminal methionine. This G-CSF molecule, designated N-methionyl-G-CSF or rmet(hu)G-CSF, received the international non-proprietary name (INN) "filgrastim" and has a molecular weight of 18.7-18.9 kD (Welte 1996). The theoretical relative mass of filgrastim (Mr) is 18.799. The G-CSF polypeptide chain contains five cysteines and structural investigations with filgrastim revealed two disulfide bonds between Cys 37-43 and Cys 65-75, while the unpaired Cys 18 remains reduced (Wingfield 1988). The first product on the market was Amgen's Neupogen® containing filgrastim, an *E. coli*-expressed, recombinant human met-G-CSF (Welte 1996). Another G-CSF product, approved in the European Union, Chugai's Granceyte®, containing lenograstim, is derived from recombinant mammalian (CHO) cells and is glycosylated (Holloway 1996). In addition, Amgen launched in 2002 an improved version of G-CSF, Neulasta®, which consists of a conjugate filgrastim and polyethylene glycol (INN pegfilgrastim) (Molineux 2004). Finally, several biosimilar versions of Neupogen® were launched in Europe by different generic pharmaceutical companies during the last years.

Overexpression of heterologous recombinant polypeptides in transformed microorganisms often results in the formation of so-called inclusion bodies (IBs), which contain the recombinant protein. These inclusion bodies are highly refractile, amorphous aggregates and the polypeptides therein are generally unfolded, reduced, inactive, and at least partially insoluble in common aqueous buffers. Processes for obtaining recombinant proteins from inclusion bodies are described in the art and generally comprise lysis and disruption of the cells followed by centrifugation. The pellet comprising a large proportion of inclusion bodies is usually washed with detergents to remove lipid membranes, lipopolysaccharides (LPS) and other cell debris or contaminants.

The scientific literature provides many methods how such inclusion bodies can be isolated from bacteria and purified and how the recombinant protein afterwards can be solubilised and refolded into its native state. (The terms 'refolding' and 'renaturation' are synonymously used herein).

Different strategies have been used to solubilise the recombinant protein. Besides ionic or non-ionic detergents, such as sodium dodecyl sulfate (SDS) or N-laurylsarcosin (sarkosyl), chaotropic reagents, such as guanidine hydrochloride (GuHCl) or urea, have been used to solubilise a protein of interest. Often the solubilisation is performed under alkaline conditions (pH 8-12.5) in presence of reducing agents, such as dithiothreitol (DTT), dithicerythrol (DTE) or 2-mercaptoethanol (ME) (Marston 1986, Rudolph 1990, Rudolph 1996, Dietrich 2003). Typically, the solubilised protein is at first fully reduced and inactive; and then undergoes refolding prior to the chromatographic purification.

For example, EP0219874 discloses generic methods for refolding of recombinant proteins from *E. coli* inclusion bodies. For the solubilisation the chaotropic agents GuHCl and arginine were used at high pH. EP0219874 describes the formation of disulfide bridges under redox conditions provided by GSH/GSSG.

Rudolph 1990 describes the following sequence of steps: a) the use of GuHCl or urea for solubilisation at pH 8-9 under reductive conditions (DTT, DTE or 2-ME), b) removal of reagents by dialysis or gel chromatography (Sephadex G-25) and c) disulfide formation (=refolding) by oxido shuffling systems or by reversal chemical modification of protein thiols, both based on the effect of added GSH/GSSG.

Another review (Rudolph 1996) put emphasis on additives used during refolding which can affect the solubility and stability of the unfolded protein, the folding intermediates and the native folded protein. The authors suggest a generic basic protocol for solubilisation and refolding: Solubilisation with 6M GuHCl and 100 mM DTT at pH 8. Reducing agents are removed by dialysis and pH is adjusted to 4.5. Folding is performed by high dilution (1:200) in a buffer with EDTA and GSH/GSSG, at pH 7.5 to 8.5.

Dietrich 2003 describes the solubilisation of proteins from *E. coli* inclusion bodies with 6M GuHCl under reductive conditions (DTE). The refolding incubation was defined at pH 9 in 1 M arginine in presence of GSH/GSSG. Final purification was performed using hydrophobic interaction chromatography (HIC) followed by cation exchange chromatography (CEX) using SP Sepharose.

An application note available from GE Healthcare 2007 (Application Note 18-1112-33, 1-4) also reviewed general protocols. Solubilisation is recommended with 8M urea or 6M GuHCl. Refolding was mentioned as slow dialysis or dilution near neutral pH. Alternatively a chromatographic step can be used for refolding. The suggested chromatographic methods comprise size exclusion chromatography (SEC), ion exchange chromatography (IEX) and hydrophobic interaction chromatography (HIC) which is suggested instead of dialysis or dilution.

WO00/02901 describes a general method for refolding by applying high pressure within a refolding tank. Optionally, chaotropic agents and/or redox compounds (DTT/GSSG) are present in the refolding buffers.

Starting in the 1980s there is a long history of developing methods for producing biologically active recombinant G-CSF. The majority of publications describe production in *E. coli*. In this host, G-CSF is well-expressed and accumulates normally in inclusion bodies. Other expression systems used were for example CHO cells (Holloway 1994), human cells (WO01/04154), or yeast (U.S. Pat. No. 5,055,555).

Zsebo 1986 described the solubilisation of G-CSF with 2% sarkosyl and the purification of soluble G-CSF by AEX and CEX chromatographies.

WO87/01132 describes *E. coli*-derived human G-CSF (filgrastim). Two alternative methods for refolding/purification were described: Process 1): G-CSF was solubilised with 1% lauric acid (a saturated C15 fatty acid) and oxidized with 40 µM CuSO4 followed by HPLC-purification on a C4 material. Process 2): Solubilisation was performed with 2% sarkosyl and oxidation with 20 µM CuSO4. The G-CSF was precipitated with acetone, again solubilised with 6M GuHCl and by this condition unfolded. After removal of GuHCl by gel chromatography (Sephadex G-25, a refolding step) the subsequent chromatography was CEX (CM-Cellulose) followed by a final size exclusion chromatography (SEC, Sephadex G-75).

An alternative solubilising agent was used by Devlin 1988, which solubilised the IB-pellet with 10% SDS and purified the SDS-loaded G-CSF by SEC (Sephacryl S-200 in 0.1% SDS) followed by reversed-phase high pressure liquid chromatography (RP-HPLC, Vydac C4).

These early publications focused on constructing suitable expression systems and getting purified substance for further characterizing of G-CSF, rather than providing refolding and purification processes suitable for commercial large scale production of recombinant G-CSF. A more advanced process was published in WO89/10932, which describes methods for purification of human and bovine G-CSF from *E. coli* IBs. The IBs were treated with detergents (deoxycholate) to extract contaminants. Sarkosyl was used to solubilise G-CSF. Oxidation was performed, with CuSO4. Further processes were described in Lu 1992 and Heidari 2001.

Several alternatives to the above mentioned methods for solublisation and oxidative refolding, including the method of WO89/10932 using 2% sarkosyl/40 µM CuSO4, have been published. Most of these strategies followed the classical general approach of solubilisation (Marston 1986, Rudolph 1990, Rudolph 1996, see above), using strong denaturants such as GuHCl and urea, completely breaking the hydrogen bonds under reductive conditions at alkaline pH. Especially the more recent publications preferred the refolding of GuHCl— or urea-solubilised G-CSF.

For example, Wingfield 1988 describes the purification of a wild-type G-CSF and a mutein from *E. coli* IBs. Solubilisation was performed with 6M GuHCl. A first purification was done with unfolded protein on SEC (Sephacryl S200) in presence of 4M GuHCl. G-CSF was then oxidized and refolded by dialysis against 3 M urea and further purified with CEX (CM-Sepharose) and SEC (Ultrogel AcA54).

A paper from Kang 1998 described N-meth-hu-G-CSF expression in *E. coli* IBs. G-CSF was solubilised with 2M urea under alkaline conditions. Refolding was initiated by dilution and incubation for 16 h at room temperature. Then the pH was lowered to pH 5.5 and the emerging precipitates were removed. Two subsequent chromatographies were performed, a CEX step (SP Sepharose) was followed by a chromatofocusing step (PBE94) using polybuffers.

WO98/53072 discloses a G-CSF bearing a small leader peptide at the N-terminus which was expressed in *E. coli* without cleavage of the signal peptide and thus accumulated in IBs. Solubilisation was performed in 8M urea under reductive conditions (10 mM DTT). The solubilised. G-CSF was subjected to AEX (DEAE-Sepharose) followed by SEC (Sephacryl 200). An oxidative refolding was described which comprises a rather short incubation in presence of 2 mM GSH.

In another publication (Wang 2005) the inclusion bodies were solubilised with 8M urea in presence of 100 mM 2-ME, and 5 mM EDTA at pH 8. A matrix-bound refolding was performed during the subsequent AEX chromatography (Q-Sepharose). G-CSF was bound to the column and while staying bound the urea concentration in the mobile phase was lowered. The buffer contained GSH/GSSG and the eluted G-CSF was biologically active. Further methods are described in WO01/87925 and WO02004/015124.

WO2004/001056 discloses a method comprising a first incubation at pH 8 for 6 hours followed by a second incubation at pH 4-5 for 6-8 hours.

WO2006/097944 describes that IBs are solubilised with urea or GuHCl (2-6M) at alkaline pH (8-11) and the refolding was performed after dilution at acidic ph for 6-16 h at room temperature.

WO2006/135176 deals with G-CSF muteins which were purified for subsequent PEGylation. The G-CSF variants were expressed in *E. coli* and solubilised from IBs by using 8M urea at pH 11. Refolding was performed by diluting to 2M urea and 50 mM glycine and incubated at pH 9 over night.

EP1630173 discloses methods for isolating and refolding of G-CSF (filgrastim) from *E. coli* IBs. The methods are based on extraction with denaturants, preferentially GuHCl. Refolding was performed in the presence of GSH/GSSG, high pH and low temperatures.

EP1837346 describes methods for isolating, refolding and purifying G-CSF (filgrastim) expressed in *E. coli* IBs. GuHCl was used for solubilisation and the refolding was performed in presence of GSH. A subsequent gel chromatography (Sephadex G-25) was applied for removal of denaturants and buffer.

Rao 2008 describes a process for the production of G-CSF from *E. coli* IBs. The IBs were dissolved in 2M urea in presence of 25 mM cysteine at unusually high pH values (pH 12-12.8).

Similar methods for solubilisation, refolding and purification of G-CSF (filgrastim) were described by Vanz 2008.

Khalilzadeh 2008 suggested modifications to the method using sarkosyl/CuSO4 described above. The solubilisation of washed IBs was performed with 8M urea. Refolding was performed by step dialysis to reduce the urea from 8M to 0M. CuSO4 concentration ranged from 5-60 μM, and an optimum was shown for 40 μM. The chromatographic sequence consists of three steps, AEX (DEAE) followed by HIC (Butyl) and a final SEC (Sephadex G-25).

WO2008/096370 also describes refolding and purification of huG-CSF from *E. coli* IBs. G-CSF was solubilised with urea in presence of DTT and pH was raised to pH 12-12.5.

Finally, WO2010/146599 discloses solubilisation of G-CSF with 6M GuHCl and reduction with DTT. For refolding a complex buffer was composed consisting of 2M urea, 0.1M arginine, 10% sucrose, 2 mM EDTA and including oxido-shuffling agents such as 10 mM Na-ascorbate/dihydroascorbate/DTT or GSH/GSSG or cysteine/cystine (redox).

There is an ongoing need for new methods for obtaining G-CSF from inclusion bodies.

SUMMARY OF THE INVENTION

The invention relates to new methods for the refolding of recombinant granulocyte colony stimulating factor (G-CSF) extracted from inclusion bodies into biologically active molecules. The methods comprise the solubilising of G-CSF with a solubilising agent, the oxidizing and partially refolding of G-CSF in the presence of such a solubilising agent, the efficient removal of the solubilising agent, and the completion of refolding in the absence of a solubilising agent. Various methods are disclosed for separating the solubilising agent from partially refolded G-CSF.

The inventors have surprisingly found that the combination of two refolding steps increases the yield for correctly folded G-CSF significantly.

New methods for the refolding of recombinant granulocyte colony stimulating factor (G-CSF) from inclusion bodies are disclosed. The methods comprise two refolding steps. In particular, the methods comprise the solubilising of G-CSF with a solubilising agent, the oxidative refolding (first refolding step) of G-CSF in the presence of the solubilising agent and an oxidizing agent, the efficient removal of the solubilising agent, and a second refolding step to complete the folding of G-CSF in the absence of the solubilising agent. Various methods are described for the efficient removal of the solubilising agent from partially refolded G-CSF. The invention further provides processes for subsequent purification of refolded G-CSF using ion exchange chromatography.

All cited references are incorporated herein in their entirety.

In one aspect the invention provides a method for refolding granulocyte colony stimulating factor (G-CSF) from inclusion bodies, comprising:
a) solubilising G-CSF in the presence of a solubilising agent;
b) performing an oxidation and first refolding step, comprising incubating the solubilised G-CSF in the presence of an oxidizing agent and the solubilising agent;
c) removing the solubilising agent by ion exchange resin adsorption and/or ion exchange chromatography, and optionally performing an acid precipitation; and
d) performing a second refolding step, comprising diluting and incubating the G-CSF of step (c) in the absence of solubilising agent.

The inclusion bodies can be obtained from a microorganism, preferably from *E. coli*. The G-CSF may be recombinant bovine or human G-CSF, it can be bovine or human methionyl-G-CSF. The solubilising agent may be N-Lauroyisarcosin. The oxidizing agent may be $CuSO_4$. The solubilisation of G-CSF may be performed at a pH value greater than ph 7.

In some embodiments, the solubilising agent is N-Laurcylsarcosin at a concentration of about 0.5% to about 1.5%.

In some embodiment, the oxidation and first refolding step is performed for at least two hours. In some embodiments, the oxidation and first refolding step is performed under airflow and without cooling. In some embodiments the oxidation and first refolding step is performed at a pH value of about 7-9 and at a temperature of about 20-28° C. for about 15-25 hours.

In some embodiments the removal of the solubilising agent in step (c) above comprises: AEX (anion, exchange) and CEX (cation exchange), optionally in this order. In some embodiments, the removal of the solubilising agent in step (c) above comprises:
a) binding to an anion exchange resin material by mixing the G-CSF solution with the suspended resin material and removal of the resin material by filtration, and/or
b) ion exchange chromatography under conditions where the solubilising agent binds to the resin and G-CSF remains in the flow through and/or,
c) ion exchange chromatography under conditions where G-CSF binds to the resin and the solubilising agent remains in the flow through.

In some embodiments the solubilising agent and other impurities are removed by the sequential application of the following steps: AEX, acid precipitation, AEX, and CEX.

In some embodiments, the solubilising agent and other impurities are removed by the sequential application of the following steps:
a) binding of the solubilising agent to an anion exchange resin material by mixing the G-CSF solution with the suspended resin material and removal of the resin material by filtration;
b) precipitation of impurities by lowering the pH below pH 5 and by removal of the precipitate by filtration;
c) anion exchange chromatography conducted under conditions wherein the residual solubilising agent binds to the resin and G-CSF remains in the flow through;
d) cation exchange chromatography conducted under conditions wherein G-CSF binds to the resin and the residual solubilising agent remains in the flow through; and
e) elution of bound G-CSF from the cation exchange resin by step or gradient elution using an elution buffer with increased pH or salt concentration.

In some embodiments of the methods described herein, the second refolding step is performed in a low conductivity buffer and/or under cooled conditions and/or for more than 12 hours. In some embodiments the second refolding step is performed at a conductivity below 2.0 mS/cm, and/or at a temperature of about 2-8° C. and/or for at least 24 hours. In some embodiments, the second refolding step is performed at a pH value above pH 7.

In some embodiments, the methods described herein further comprise a polishing step, which comprises one or more ion exchange chromatographies. The one or more ion exchange chromatographies in the polishing step may comprise an anion exchange chromatography followed by a cation exchange chromatography.

In another aspect, the invention provides a process for purification of G-CSF and/or removal of a solubilising agent used for solubilisation of G-CSF from inclusion bodies comprising the following steps:

a) anion exchange chromatography conducted under conditions where G-CSF binds to the resin;
b) elution of bound G-CSF by step or gradient elution using an elution buffer with decreased pH or increased salt concentration;
c) cation exchange chromatography conducted under conditions where G-CSF binds to the resin;
d) elution of bound G-CSF by step or gradient elution using an elution buffer with increased pH or salt concentration;

characterised in that the backbone polymers of the anion and cation exchange resins both comprise methacrylate derivatives.

DETAILED DESCRIPTION OF THE INVENTION

The present invention provides new methods for refolding granulocyte colony stimulating factor (G-CSF). In particular, it provides new methods for obtaining active G-CSF from inclusion bodies at high yield, which allows the industrial production of purified G-CSF.

One aim of the present invention was to provide an effective production process at an industrial scale for a recombinant G-CSF drug substance of high purity (up to pharmaceutical grade), considering quality, economy and regulatory needs. The present invention provides a novel method for refolding and purification of recombinant G-CSF expressed in inclusion bodies.

The prior art describes several methods for solubilising and refolding G-CSF from inclusion bodies. As outlined above (see Background) the prior art on solubilising and refolding IB proteins and in particular with respect to G-CSF) can be divided into two different main strategies. The more classical approach is the use of a strong chaotropic agent (denaturant) such as urea or GuHCl, typically under reductive conditions and alkaline pH. The second strategy, which is also commonly used in the field, is the use of a strong surfactant, such as sarkosyl or lauric acid for solubilisation. Sporadically also the use of sodium dodecylsulphate (SDS), a strong ionic detergent, for solubilising of G-CSF was reported (Devlin 1988).

Each of the prior art methods has certain disadvantages. As demonstrated in experiments performed by the inventors, SDS as the solubilising agent was not suitable because its efficient removal was difficult, if not impossible. For example, when removing SDS by chromatography on ceramic hydroxy apatite (CHT), trace amounts of SDS remained bound to the protein. SDS could not be removed completely. Solubilisation with GuHCl (Wingfield 1988, Dietrich 2003, WO2006/097944, EP16301273, EP1837346, WO2010/146599) is problematic for other reasons. While GuHCl can be removed by dialysis or gel chromatography, the GuHCl solubilisation method subsequently requires large volumes caused by the need of strong dilution to prevent the aggregation of folding intermediates (Rudolph 1990, Rudolph 1996) during the refolding incubation. Dilutions of up to 1:200 were reported (Rudolph 1996). In GuHCl methods tested by the inventors, the requirement for strong dilution was confirmed and at least a dilution ratio of 1:50 was required for optimal yields using the GuHCl method. This kind of solubilisation would require big stainless steel tanks for large scale processes which is uneconomic.

Instead of GuHCl another denaturant, urea, has been reported for use in solubilisation of G-CSF. Nearly saturated concentrations such as 8M urea were applied in the prior art (WO96/53072, WO01/67925, WO2006/135176, Khalilzadeh 2008, WO2008096370). The same problems as discussed with respect to GuHCl apply also to urea. In addition, it is well-known to the person skilled in the art that the presence of urea, especially at alkaline pH, can favour undesired protein modification, such as deamidation. Furthermore, the presence of isocyanic acid, which can generate from ammonium cyanate (which is always in equilibrium with urea in solution), results in carbamylation of primary amino groups (Rudolph 1996). Finally, it has also been reported in the art that there may be a benefit for the yield when the aggregation inhibitor arginine is present as co-denaturant in high concentration during refolding (EP0219874, Rudolph 1996, Dietrich 2003). However, arginine is an expensive reagent and it would be economically desirable to abandon the use of arginine.

As mentioned above, the surfactant sarkosyl may also be used for the solubilisation of G-CSF from IBs. Preferentially 2% sarkosyl was used (Zsebo 1986, WO8701132, WO8910932, Lu 1992, Heidari 2001). Sarkosyl is an anionic tenside with good solubility. One advantage of using sarkosyl is the lower dilution factor (2-fold instead 50-200-fold for GuHCl/urea) required during the subsequent refolding incubation. Another advantage is the relatively low production of waste chemicals for the environment. However, when using the originally described method the present inventors observed in their experiments rather low yields after refolding in connection with a nigh batch to batch variation. Surfactants like sarkosyl generally facilitate solubilisation by increasing the solubility of proteins in general. Since sarkosyl does not denature and unfold proteins like the chaotropic agents do, initially incorrectly folded IB proteins cannot be refolded later; thus the yield should be lower when compared to the GuHCl/urea method.

The present invention overcomes the disadvantages of the prior art.

The present inventors provide a new method for obtaining refolded G-CSF, which addresses the problems associated with the prior art methods. It was surprisingly found that by using a first oxidative refolding step in the presence of a solubilising agent, followed by a step of efficiently removing the solubilising agent (for example by ion exchange resin adsorption and/or acid precipitation and/or ion exchange chromatography), followed by a second refolding step which comprises diluting the G-CSF and incubating it in the absence of solubilising agent, increased yields of monomeric soluble G-CSF can be obtained, i.e. by the methods described herein refolded G-CSF is obtained.

The present invention thus relates to new methods for producing biologically active G-CSF from inactive precursors in inclusion bodies. Overexpression of heterologous recombinant polyoeptides in microorganisms often results in inclusion body formation, wherein the polypeptides are unfolded, reduced, inactive, and at least partially insoluble in common aqueous buffers. New methods for the refolding of recombinant granulocyte colony stimulating factor (G-CSF) from inclusion bodies are disclosed herein. Particularly, this invention relates to a new refolding method comprising two refolding steps. The methods comprise the solubilising of G-CSF with a solubilising agent, the oxidative refolding (an "oxidation and first refolding step") of G-CSF in the presence of the solubilising agent and an oxidizing agent, the efficient removal of the solubilising agent, and a second refolding step to complete the folding of G-CSF in the absence of a solubilising agent.

The invention also relates to a new combination of refolding and purification steps. After a first refolding step, a novel intermediate purification step is introduced to assure efficient removal of the solubilising and oxidising agents, before the second refolding step is performed to complete the folding of G-CSF. The present invention also relates to new methods for removal of solubilising and other agents used in refolding processes in general.

The main principle of the newly described methods is schematically depicted in FIG. 1 (together with optional downstream polishing steps). Briefly, the method comprises:
a) solubilising G-CSF from inclusion bodies by using a solubilising agent (optionally preceded by extraction and/or isolation and/or washing of the inclusion bodies); and
b) oxidizing and partially refolding of solubilised G-CSF by incubation in the presence of an oxidizing agent and the solubilising agent; and
c) removing the solubilising agent (and other impurities); and
d) completion of refolding by dilution and incubation of partially refolded G-CSF.

Thus, the second refolding step is performed in the absence of the solubilising agent.

Thus, in a first aspect the invention provides a method for refolding granulocyte colony stimulating factor (G-CSF), from inclusion bodies, comprising:
(a) solubilising G-CSF in the presence of a solubilising agent; and
(b) an oxidation and first refolding step, comprising incubating the solubilised G-CSF in the presence of an oxidizing agent and the solubilising agent; and
(c) removing the solubilising agent by ion exchange resin adsorption and/or acid precipitation and/or ion exchange chromatography; and
(d) a second refolding step, comprising diluting and incubating the G-CSF of step (c) in the absence of a solubilising agent.

The inclusion bodies can be obtained from a microorganism. The microorganism may, for example, produce G-CSF recombinantly. The method may optionally thus further comprise a step of isolating the inclusion bodies from a microbial cell.

Inclusion Bodies

The present invention provides methods for refolding G-CSF from inclusion bodies. In the past, several different expression systems have been tested for their ability to produce G-CSF in high amounts. All the bacterial strains which were tested express the G-CSF protein in form of inclusion bodies (IBs). Inclusion bodies (IBs) contain G-CSF in high amounts, however, in unfolded, inactive form. Fractions of isolated, and preferably washed inclusion bodies, may be used as starting material for the methods described herein. Such inclusion body preparations can be provided by suitable expression systems, fermentation conditions, harvesting and lysing procedures, and suitable methods for isolation and washing of the IBs. Such methods are disclosed in the prior art (see for example Rudolph 1990, Rudolph 1996, Heidari 2001, Khalilzadeh 2008, Rao 2008, Vanz 2008, U.S. Pat. No. 5,849,883, EP0219874, EP1630173 or WO2004001056). Processes for extracting the inclusion bodies form the host cells generally comprise lysis and disruption of the cells followed by centrifuging. The inclusion bodies may be obtained by harvesting the cells in a separator (e.g. by centrifugation, e.g. at 11000 g), mechanically disrupting the cells with a high pressure homogenizer (e.g. at about 1000 bar) and then separating the inclusion bodies from cell debris in a separator (e.g. by centrifugation, e.g. at 11000 g). The pellet comprising a large proportion of classical inclusion bodies is usually washed with detergents. The inclusion bodies may be frozen and stored prior to solubilisation of G-CSF. IBs which were separated from cell debris in a separator and stored in reductive buffer at −80° C. were found stable up to 8 months.

The inclusion bodies may be obtained from microbial cells. The methods described herein may thus comprise a step of extracting the inclusion bodies from a microbial host cell. The microbial host cell used for expression of G-CSF can be a yeast cell, a filamentous fungus cell, or a bacteria cell. In preferred embodiments the microorganisms are bacteria, in more preferred embodiments they are gram-negative bacteria, and most preferably they are *E. coli*. The inclusion bodies may thus be obtained from an *E. coli* cell.

G-CSF

"G-CSF" as used herein in the context of the invention includes species orthologues of G-CSF, such as for example human G-CSF, bovine G-CSF, etc. The amino acid sequence of human G-CSF is (SEQ ID NO:1):

TPLGPASSLPQSFLLKCLEQVRKIQGDGAALQEKLCATYKLCHPEELVLL

GHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGG

VLVASHLQSFLEVSYRVLRHLAQP which for example can be found in Holloway, 1994, or in Drugbank Accession No DB00099.

The sequence of bovine G-CSF is (SEQ ID NO: 2):

TPLGPARSLPQSFLLKCLEQVRKIQADGAELQERLCAAHKLCHPEELMLL

RHSLGIPQAPLSSCSSQSLQLRGCLNQLHGGLFLYQGLLQALAGISPELA

PTLDTLQLDVTDFATNIWLQMEDLGAAPAVQPTQG AMPTFTSAFQRRAG

GVLVASQLHRFLELAYRGLRYLAEP which can for example be found in FIG. 7 of U.S. Pat. No. 5,849,883, or PDB Accession No: 1BGC-A.

In preferred embodiments the G-CSF is mammalian G-CSF, in particularly preferred embodiments it is human G-CSF. In some preferred embodiments the recombinant polypeptide is methionyl-G-CSF (Met-G-CSF), such as human Met-G-CSF (r-met-hu-G-CSF=filgrastim). The sequence of filgrastim is (SEQ ID NO:3):

MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQGAMPAFASAFQRRAG

GVLVASHLQSFLEVSYRVLRHLAQP

Bovine G-CSF may be equally be provided as methionyl-bovine G-CSF.

"C-CSF" as used herein in the context of the invention includes functional variants of G-CSF. Reference to "variant" herein means reference to "functional variant", unless the context indicates otherwise. A variant of G-CSF protein refers to a protein that differs from the G-CSF protein sequence, but still has the same biological activity (functional variant). A "variant" of G-CSF protein refers to a protein which differs from the reference G-CSF protein sequence (such as the human G-CSF sequence) in one or more amino acid(s). A "variant" may, alternatively or in addition, have other modifications such as, for example, methylation, pegylation, succinylation, addition of tags or labels, etc. the variant may be an enzymatically or chemically modified G-CSF. It may be a fusion protein fused to another peptide or polypeptide.

In preferred embodiments, the G-CSF is pegylated.

"Variants" may be natural variants, including allelic variants or splice variants (see for example Zsebo 1986), including allelic variants, or synthetically generated variants. It was shown in the prior art that modified forms of G-CSF are expressed in inclusion bodies. For example, EP0719860 describes in examples 2 and 3 the construction and production of modified bovine G-CSF, which are expressed in inclusion bodies. Variants can thus be obtained using the methods described herein.

In some embodiments, the G-CSF variant is a protein sharing at least 70%, at least 80%, at least 90%, at least 91%, at least 92%, at least 93%, at least 94%, at least 95%, at least 96%, at least 97%, at least 98%, at least 99%, or at least 99.5% sequence identity with SEQ ID NO:3 (r-met-hu-G-CSF=filgrastim). Sequence identity can be determined using standard sequence analysis tools, such as for example Clustal, BLAST, etc. or alignment algorithms such as for example Needleman-Wunsch algorithm, Smith-Waterman algorithm, etc. The variant may have one or more conservative amino acid substitution(s). An amino acid substitution, is conservative, if one amino acid is exchanged with an amino acid having similar properties, for example a polar amino acid with another polar amino acid, an acidic amino acid with another acidic amino acid, etc. Conservative substitutions are less likely to affect the chemical properties and thus the function of the protein. "Variants" to G-CSF thus include proteins having one or more mutation(s), deletion(s), substitution(s), insertion(s) and/or modification(s) of one or more amino acid compared to SEQ. ID NO:3, as long as the variant of G-CSF still exhibit the same biological function than G-CSF (functionally equivalent). Whether a variant has the same biological function can be tested in assays determining the biological activity of G-CSF (as discussed below). Commercially available G-CSF may be used as a reference control. A variant can be considered to have the "same biological activity", i.e. to be "biologically active" or "active" if it has at least 80%, at least 85%, at least 90%, at least 91%, at least 92%, at least 93%, at least 94%, at least 95%, at least 96%, at least 97%, at least 98%, at least 99%, or at least 99.5% of the activity of the commercially available G-CSF reference.

Reference to "G-CSF" herein thus includes reference to species orthologues and variants, i.e. functional variants, of human G-CSF.

Solubilisation

The G-CSF of the IB fraction is solubilised in the presence of a solubilising agent. Any suitable solubilising agent (i.e. any agent that leads to solubilisation of G-CSF as described herein) may be used. Such solubilising agents can be selected from, for example, (but are not limited to) the group of a denaturant or a chaotropic agent, such as for example (but not limited to) GuHCl or urea, or the group of a detergent, a tensile or a surfactant, such as for example (but not limited to) N-lauroylsarcosin (sarkosyl), lauric acid, sodium dodecyl sulphate (SDS) or N-cetyltrimethylammonium chloride.

With regard to sarkosyl, the present inventors found that contrary to the frequently reported concentration of 2% sarkosyl, maximum solubilisation is already achieved at 1% (w/v) sarkosyl. More advantageously, in contrast to other ionic detergents like SDS, it was found by the present inventors that sarkosyl can be removed completely from the product with a variety of purification methods. Finally, it was found by the present inventors that a second refolding step after efficient removal of sarcosyl leads to increased, yields of correctly folded monomeric G-CSF.

Accordingly, in preferred embodiments the present invention the solubilising agent is a detergent or surfactant. In more preferred embodiments the solubilising agent is an anionic surfactant, and most preferably it is sarkosyl. The preferred concentration of sarkosyl during solubilisation is 0.2-2.0% (w/v), in more preferred embodiments about 0.5%-1% (w/v) and most preferably about 1% (w/v) or 1% (w/v).

It was further found that optimisation of other parameters such as temperature, pH, buffer etc. may further improve the yield. Optimal temperature, pH, buffer etc. can be established in light of the present description using the methods described herein. In preferred embodiments, the solubilisation is performed at an alkaline pH, such as for example at a pH within the range of from 7 to 10, or from 7 to 9, or from 7.5 to 8.5, or from 7.8 to 8.2. In preferred embodiments, the pH is about 8 or is 8. In some embodiments the solubilising is performed at room temperature, i.e. between 20-25° C. Suitable buffers to be used at particular pH ranges for solubilisation are known in the art. For example, Tris-HCl may be used. Preferably, solubilisation is performed under stirring.

In preferred embodiments, the solubilising is performed with sarkosyl at alkaline pH, preferentially pH 8. The preferred buffer for the solubilisation is Tris-HCl/pH 8, preferentially 40 mM Tris-NCl/pH 8.

After the solubilisation, a dilution step may be performed, such as for example a dilution of five-fold, or four-fold, or three-fold or preferably two-fold. The preferred solvent for dilution is a low conductivity buffer or more preferably just water. Low conductivity means a conductivity of at least below 2 mS/cm, more preferably below 1 mS/cm. A suitable buffer system is for example Tris/HCl at concentrations of 10 mM Tris or below with a pH value greater than 7. Other buffers with the same low conductivity and pH may also be used.

First Refolding (Oxidative Folding)

Oxidation the reduced cysteines and disulfide formation is necessary for correct folding of G-CSF. The classical approach is the oxidisation in the presence of a pair reducing/oxidizing agent (Rudolph 1990, Rudolph 1996, see Background). Numerous in-vitro refolding techniques have been published. Based on these refolding protocols the present inventors have derived some general principles which are common for disulfide-containing proteins expressed in inclusion bodies. Because the proteins are in a reduced state and unfolded the mechanism behind such a refolding procedure is primarily an oxidative folding of the polypeptide chain into the native conformation by forming the natural disulfide bridges between the sulfhydryl groups of cysteine pairs. In a typical refolding process the concentration of the solubilising agent (chaotropic agent or detergent) is at first decreased below denaturing concentrations often by step-wise dilution or by dialysis or by gel chromatography, for instances using Sephadex G-25. The presence of an oxidant such as $CuSO_4$ or a redox system such as glutathion red/ox (GSH/GSSG) promotes the disulfide formation during the refolding incubation. Generally the incubations were performed at room temperature for several hours up to days. Various additional additives were described which can optionally be used to increase solubility of the protein and/or to prevent aggregation. Aggregation, especially of partially folded intermediates, is a major problem during refolding and is at best prevented by dilution below critical protein concentration levels (Rudolph 1990, Rudolph 1996). For G-CSF the prior art also teaches the oxidation by use of CuSO4 in combination with sarkosyl. The refolding was performed in presence of oxidising agent and solubilising agent (Zsebo 1986, WO8701132, WO8910932, Lu 1992, Heidari 2001).

The inventors found that in the presence of solubilising agent, such as sarkosyl, the folding of G-CSF was not fully achievable. Such an oxidation and folding step thus only leads to a partial refolding of G-CSF. The inventors have found that complete removal of the solubilising agent followed by a second folding step in the absence solubilising agent leads to improved yield. The present inventors also devised optimised methods for removal of the solubilising agent (see below). Other contaminants, which may also contribute to the incomplete folding, are also removed.

Any suitable oxidizing agent may be used, such as oxygen or air flow (bubbling), GSSG (Glutathion-ox), metal ions ($Cu^{2+}$, $Fe^{2+}$, $Zn^{2+}$, . . . ) peroxide ($H_2O_2$). In preferred embodiments, the oxidation agent is $CuSO_4$. Besides $CuSO_4$ also other copper salts can be used (e.g. $CuCl_2$).

The solubilising agent is used in an effective amount. The skilled person can readily determine and optimise the effective amount, i.e. the amount of solubilising agent that achieves efficient solubilisation of G-CSF. Methods to determine the amount of solubilised G-CSF are described further below (see for example Example 13.3).

The preferred concentration of the solubilising agent during the first refolding step is 0.2-2.0% (w/v), more preferably it is 0.2%-1% (w/v) and most preferably is about 0.5% (w/v) or 0.5% (w/v). If sarkosyl is used, in preferred embodiments, the concentration of sarkosyl is below 1% (w/v) preferentially 0.5% (w/v).

The present inventors further observed that long oxidation periods can result in the appearance of 2-3 extra peaks in the RP-HPLC chromatograms. These additional peaks are likely due to the oxidation of the methionine residues of G-CSF. Such oxidative forms are undesired product-related substances and their removal by suitable chromatography is difficult.

In some embodiments the oxidative refolding (i.e. the oxidation and first refolding step) is performed for a period of 1-30 hours, or 2-25 hours, or 6-25 hours, or 10-25 hours, or 12-25 hours, or 14-25 hours, or 16-25 hours, or 18-22 hours, or 19-21, or 20-24 hours. In some embodiments the oxidation and the partially refolding of G-CSF is performed for more than two hours, preferentially for more than twelve hours, preferably for more than 20 hours, most preferably for 20-24 hours.

In preferred embodiments, the oxidative refolding step (i.e. the oxidization and first refolding step) is performed at an alkaline pH, such as for example at a pH within the range of from 7 to 10, or from 7 to 9, or from 7.5 to 8.5, or from 7.8 to 8.2. In preferred embodiments, the pH is about 8 or is 8. In some embodiments the pH value of the first refolding step is more than pH 7, preferably pH 8.

The oxidative refolding step may also be performed using G-CSF that is already (partially) purified. In some embodiments the G-CSF which is used for the oxidative refolding, has a purity of greater than 50%, preferentially a purity of about 60-70%, or even higher.

The oxidative refolding preferably is performed without cooling, preferably at room temperature, preferably at 18-30° C., preferably at 20-28° C., preferably at 20-26° C., preferably at 20-24° C., preferably at 21-23° C., most preferably at about 22° C. or at 22° C.

The oxidative refolding may be performed under continuous airflow.

The most preferred conditions for the oxidative refolding (oxidation and first refolding step), based on various optimisation experiments, are those shown in Table I under the column "1st Refolding".

The oxidative refolding step may be stopped by addition of a stopping agent, such as for example EDTA. In some embodiments the oxidation is stopped by addition of EDTA, preferably at a final concentration of about 1 mM, but other concentrations may be used. EDTA removes the $Cu^{2+}$ ions (in case CuSO4 is used as an oxidizing agent), thereby stopping the oxidation. Other $Cu^{2+}$ complexing agents than EDTA and/or other concentrations may be used. Depending on the oxidizing agent, other chelators may be used, such as terdentat-ligands, such as N-picolinoyl-ethylenediamine, glycine-2-pyridylmethylamide, $N^{\alpha}$-(2-pyridylmethyl)-glycinamide and $N^{\alpha}$-(2-pyridylmethyl)-glycine-ethylamide.

As discussed above the inventors have found that the presence of sarkosyl prevents significant portions of G-CSF from becoming fully refolded. The inventors consider that this may in part be caused by slower refolding in the presence of the solubilising agent. However, as discussed above the incubation time cannot be extended at will, because the quality of the product can reach unacceptable levels at longer incubation times.

The inventors have surprisingly found that the refolding can be optimised and completed by a second incubation, after complete removal of the solubilising and oxidative agents, which unexpectedly resulted in higher yields of soluble, pure, biologically active G-CSF.

Removal of Solubilising and Oxidising Agent and Removal of Other Contaminants

In an intermediate purification step, the oxidized and partially refolded G-CSF is further purified. Importantly, the solubilising agent must be removed completely, before the second refolding step is performed. Also the oxidising agent and partially further contaminants/impurities are being removed.

Several procedures are described in the prior art for removal of solubilising and oxidising agents either by dialysis/ultrafiltration or by chromatographic methods. However, the inventors have found that by a single batch adsorption step complete removal of the solubilising agent, such as sarkosyl, cannot be achieved. In experiments performed by the inventors, sarkosyl remained in concentrations of 0.01-0.04 mg/ml after this step (Table III), which was found to negatively influence the yield of correctly folded G-CSF.

To improve the yield of soluble active G-CSF, the solubilising agent must be completely removed, i.e. below the detection levels of the detection methods described herein. For example, the concentration, of residual solublising agent may be measured, by HPLC and detection by UV. The detection limit in the assay performed by the inventors was 0.01 mg/ml. The method is described in more detail in Burgess, R. R. 1996. Purification of over produced *E. coli* RNA polymerase factors by solubilizing inclusion bodies and refolding from sarkosyl. Methods Enzymol. 273:145-149.

Any suitable removal method may be used. For example, sufficient removal can be achieved by ion exchange resin adsorption, and/or acid precipitation, and/or ion exchange chromatography. Applying any one or a combination of these techniques in accordance with the invention results in a concentration of the solubilising agent, such as sarkosyl, which will not interfere with or inhibit refolding in the second refolding step, preferably below 0.01 mg/ml, preferably below detection limit. These purification steps may be applied in any order and/or in any combination, as long as it leads to a complete removal of the solubilising agent. Other suitable purification methods may also be used. The methods described herein thus comprise a step of completely removing the solubilising agent. I.e. the solubilising agent is removed to a sufficient extent that any residual amounts do not interfere or inhibit the second folding step. The second refolding step is thus performed in the absence of the solubilising agent, i.e. the solublising agent is present in an amount which does not interfere with the second refolding step, i.e. the solubilising agent is below the detection limit.

In one embodiment of the invention, there is provided a method wherein the solubilising agent is removed by one or more of the following steps:
   i) binding to an anion exchange resin material by mixing the G-CSF solution with the suspended resin material and removal of the resin material by filtration, and/or
   ii) ion exchange chromatography under conditions wherein the solubilising agent binds to the resin and G-CSF remains in the flow through or, vice versa, G-CSF binds to the resin and the solubilising agent remains in the flow through.

In one embodiment of the invention there is provided a method wherein the solubilising agent (and other impurities) is removed by one or more of the following steps:
   i) binding to an anion exchange resin material by mixing the G-CSF solution with the suspended resin material and removal of the resin material by filtration, and/or
   ii) acid precipitation.

In one embodiment of the invention there is provided a method wherein the solubilising agent (and other impurities) is removed by one or more of the following steps:
   i) binding to an anion exchange resin material by mixing the G-CSF solution with the suspended resin material and removal of the resin material by filtration, and/or
   ii) acid precipitation, and/or
   iii) ion exchange chromatography under conditions wherein the solubilising agent binds to the resin and G-CSF remains in the flow through or, vice versa, G-CSF binds to the resin and the solubilising agent remains in the flow through.

In a preferred embodiment the solubilising agent (and other impurities) is removed by the sequential application of the following steps:
   a) binding of the solubilising agent to an anion exchange resin material by mixing the G-CSF solution with the suspended resin material and removal of the resin material by filtration
   b) precipitation of impurities by lowering the pH below pH 5 and by removal of the precipitate by filtration
   c) anion exchange chromatography conducted under conditions wherein the residual solubilising agent binds to the resin and G-CSF remains in the flow through
   d) cation exchange chromatography conducted under conditions wherein G-CSF binds to the resin and the residual solubilising agent remains in the flow through
   e) elution of bound. G-CSF from the cation exchange resin by step or gradient elution using an elution buffer with increased pH or salt concentration.

Ion exchange Resin Adsorption

Ion exchange resin adsorption may be used to remove the solublising agent.

As a first step of removing the solubilising agent an ion exchange resin adsorption may be performed. Suitable methods are known in the art. As described above, for the removal of solubilisng agent, such as sarkosyl, one method is a batch adsorption to Dowex anion exchange resins (Dow Chemicals, USA), preferably with Dowex 1X4 (WO8910932, Lu 1992, Heidari 2001). The resin capturing the bound surfactant is removed by filtration. Very similar products to Dowex resins are BioRad's AG resins (such. as AG-1X8), which can be used in the same way.

The methods described above apply to all those solubilising agents which are charged in solution. Many surfactants are amphiphilic, others are anionic or cationic. Depending on the kind of solubilising agent and the pH value of the solution the charges can be positive or negative. The use of an AEX material such as Dowex or AG-1 depends on negatively charged solubilising agents, for example sarkosyl or SDS. In contrast the ion exchange chromatography according the selection of the type of resin, can bind both, negatively or positively charged solubilising agents. Negatively charged solubilising agents will bind to AEX resins but not to CEX resins. Positively charged agents behave vice versa. For example agents such as cationic lipids, cetyl trimethyl ammonium, or arginine can be removed by cation exchange chromatography. Besides the solubilising agent also other contaminants will be at least partially removed by the methods. These other contaminants impurities may comprise process-related impurities such as for example host-cell proteins (HCP), DNA/RNA, endotoxins (for example LPS), oxidising agents (for example $Cu^{2+}$), process-related chemicals (for example EDTA), and product-related impurities, such as for example aggregates.

In some embodiments the solubilising agent is an anionic detergent or tenside which is adsorbed to an AEX resin, in a batch mode. Preferably the detergent or tenside is sarkosyl. In some embodiments the sarkosyl is adsorbed to an analytical grade (AG) AEX resin (BioRad, USA), preferably a resin of the AG. 1-X series, most preferably the resin is AG 1-X8. In some embodiments the resin is used as disposable material.

In preferred embodiments, the batch adsorption of the solubilising agent with AG 1-X resin is performed in buffers with alkaline pH, preferentially about pH 8. Suitable buffer systems can be based on phosphate, carbonate, borate, Tris, HEPES, MOPS, HEPPS, EPPS, CAPS, CAPSO, CHES, TES, BES, TAPS, Ethanolamine, Diethanolamine, Triethanolamine, Tricine, Bicine, Acetamidoalycine, Glycinamide or other biocompatible buffer substances having a pKa above 7. A preferred buffer for the adsorption is Tris-HCl/pH 8, preferentially 20 mM Tris-HCl/pH 8. Most preferred is Tris-HCl/pH8+1 mM EDTA.

Preferably the amount of AG 1-X8 is 10-60 g dry resin per gram sarkosyl, most preferably 20 g/g sarkosyl. In some embodiments the initial sarkosyl concentration is 0.5%.

In preferred embodiments, the ion exchange resin adsorption step removes more than 90%, more than 95% more preferably more than 96%, more preferably more than 97%, more preferably more than 98%, more preferably more than 99%, more preferably more than 99.2%, more preferably more than 99.3%, more preferably more than 99.4%, more preferably more than 99.5%, more preferably more than 99.6%, more preferably more than 99.7%, more preferably more than 99.8%, more preferably more than 99.9% of the solubilising agent. In preferred embodiments, the solubilising agent is sarkosyl. In some embodiments, the ion exchange resin adsorption step removes more than 95% of the sarkosyl by AG 1-X8 batch adsorption; more preferably at least 99% of sarkosyl. In some embodiments the AG 1-X8 resin with the captured sarkosyl is separated, from the solution by filtration. Preferably the filtration step makes use of 100 μm stainless steel meshes. More preferably the filtration step makes use of 100 μm nylon bag filter meshes.

If the Ion exchange resin, adsorption step does not result in sufficiently complete removal of the solubilising agent, further purification steps, such as acid precipitation and/or ion exchange chromatography can follow.

Acid Precipitation

Optionally, an acid precipitation step may be performed to remove other potential contaminants. Surprisingly the inventors found that by simple acid precipitation a significant portion of contaminants can easily be removed. G-CSF, especially filgrastim, is known to have best solubility and stability at acid pH and even remains soluble by decreasing the pH below the isoelectric point (pI of filgrastin=5.65). Acid precipitation of contaminants may be performed by lowering the pH to a value of between 6.5 and 6.0, between 6.0 and 5.5, between 5.5 and 5.0, between 5.0 and 4.5, between 4.5 and 4.0, between 4.4 and 3.5, between 3.5 and 3.0, etc.

Despite the presence of residual solubilising agent, the inventors found that addition of urea can have an additional beneficial effect on the precipitation process. By decreasing the pH value, non-specific and unwanted co-precipitations of G-CSF can sometimes occur, which can lead to undesired losses in the final yields. The inventors have found that this drawback can be overcome by the use of a sub-denaturing concentration of urea added to the solution prior to pH adjustment. The urea effectively prevents co-precipitation of G-CSF. The optimisation of this step revealed best results by lowering the pH slowly and steadily with acetic acid or sodium acetate. Values of pH below 5.0 were already effective. A rather low concentration of urea, that is about 1M, is sufficient.

In some embodiments the residual sarkosyl concentration prior the acidic precipitation is between 0.01 and 0.04 mg/ml.

In some embodiments the pH value is lowered by adding concentrated sodium acetate or acetic acid. In preferred embodiments the pH value is lowered below pH 5.0, preferably below 4.8, most preferably to pH 4.3-4.5. In some embodiments the acidification is performed in presence of urea, preferably at a concentration below 3M urea, most preferably at 1M urea. In some embodiments the precipitates are removed by depth filtration.

Ion Exchange Chromatography

Ion exchange may also be used to remove the solubilising agent. The step of removing the solublising agent may comprise one or more ion exchange steps.

If the use of ion exchange resin adsorption (with or without acid precipitation) has not resulted in a complete removal of the solubilising agent, one or more ion exchange chromatography step(s) may be performed to fully remove the solubilising agent. The ion exchange step(s) may comprise an AEX and/or CEX, in any order. Any other suitable ion exchange technology may be used.

The use of ion exchange chromatography for purification of G-CSF is described in the prior art. Many processes make use of AEX and CEX, or both methods in any order, or an IEX step in combination with other chromatographic methods such as HIC, IMAC, SEC or RP-HPLC (see Background).

With respect to sarkosyl, the inventors found that if a low concentration of residual sarkosyl remained after an AEX batch adsorption and acid precipitation), it could be fully removed by a subsequent ion exchange step.

The inventors found that after the acidic precipitation step the G-CSF remains in the supernatant and the pH is below its pI. Under these pH conditions G-CSF is cationic and will bind to CEX and not to AEX resins. This was confirmed by experiments.

In some embodiments, the ion exchange step comprises an AEX followed by a CEX. The finding that AEX can be used in a non-binding mode (G-CSF in flow through) while contaminants such as residual solubilising agent or DNA bind to the resin, prompted the inventor to develop, as one embodiment of the invention, a tandem step of two columns coupled in series in the order AEX followed by CEX. The primary function of the AEX resin is to bind residual sarkosyl and the primary function of the CEX resin is just a buffer exchange (in preparation to the $2^{nd}$ refolding). The G-CSF which passes the first column then binds to the second resin and the protein can be eluted from the CEX column by suitable methods. Such methods are known to the person skilled in the art. The elution methods for desorption of bound G-CSF may comprise an increase of the salt concentration either by step elution or gradient elution or, alternatively, the elution of G-CSF can for example be achieved by increasing the pH value above the pI. Again this can be achieved either by a step elution or by a pH gradient. If, the pH step elution is applied this additionally offers the possibility for rapid buffer and pH exchange.

Suitable functional groups are known for AEX resins used for chromatography of polypeptides. These groups comprise diethylaminoethyl (DEAE), trimethylaminoethyl (TMAE), quaterny aminomethyl (Q), and quaterny aminoethyl (QAE). These are commonly used functional anion exchange groups for biochromatographic processes. Suitable commercially available products include, for example, Macro-Prep High Q, Macro-Prep DEAE, Nuvia Q (BioRad, USA), TOYOPEARL DEAE-650, TOYOPEARL SuperQ-650, TOYOPEARL QAE-550 (Tosoh Bioscience, Japan), Fractogel EMD DEAE, Fractogel EMD TMAE (Merck, Germany), Biosepra Q Ceramic HyperD, Biosepra DEAE Ceramic HyperD (Pall Corporation, USA), DEAE-Sepharose FF, DEAE-Sepharose CL-4B, Q-Sepharose FF, Q-Sepharose CL-4B, Q-Sepharose HP, Q-Sepharose XL, Q-Sepharose Big Beads, QAE-Sephadex, DEAE-Sephadex, Capto DEAE, Capto Q, Capto Q ImpRes, Source 15Q, Source 30Q, and DEAE Sephacel (GE Healthcare, USA).

In preferred embodiments, the AEX resin is DEAE. DEAE is a classical weak anion exchange group, which in the inventor's experiments showed excellent resolution and fast equilibration profiles.

Suitable functional groups used for CEX resins comprise carboxymethyl (CM), sulfonate (S), sulfopropyl (SP) and sulfoethyl (SE). These are commonly used cation exchange functional groups for biochromatographic processes. Suitable commercially available products include, for example, Macro-Prep High S, Macro-Prep CM, Nuvia S (BioRad, USA), TOYOPEARL CM-650, TOYOPEARL SP-650, TOYOPEARL SP-550 (Tosoh Bioscience, Japan), Fractogel EMD COO—, Fractogel EMD SO3- (Merck, Germany), Biosepra CM Ceramic HyperD, Biosepra S Ceramic HyperD (Pall Corperation, USA), CM-Sepharose FF, SP-Sepharose FF, S-Sepharose FE, SP-Sepharose HP, SP-Sepharose XL, SP-Sepharose Big Beads, CM-Sephadex, Capto S, Capto SP ImpRes, Source 15S, Source 30S (GE Healthcare, USA).

In preferred embodiments, the CEX resin is a resin with SP as the functional group. SP is a classical strong cation exchange group and in the inventor's experiment gave excellent resolution, fast equilibration and excellent reproducibility.

Accordingly, in some embodiments of the invention the AEX chromatography used for the removal of solubilising agent (and oxidising agent and removal of other contaminants) is performed in the non-binding mode and the resulting flow through is directly running, without any propagation, onto the subsequent column.

In preferred embodiments the two columns (AEX-CEX) are directly connected and G-CSF binds to the CEX resin.

In some embodiments of the present invention the AEX resin is a weak anion exchanger and preferably bears DEAE functional groups. Most preferably the resin is DEAE Macro-Prep (BioRad, USA).

In some embodiments the sample load is performed at a pH value below 5, preferably at pH 4.3-4.5, most preferably in a sodium acetate buffer pH 4.5.

In some embodiments of the present invention the CEX resin is a strong cation exchanger and preferably bears SP functional groups. Most preferably the resin is Toyopearl SP-650 (Tosoh, Tokio).

In preferred embodiments, the elution of G-CSF from the CEX resin is performed by increasing the pH value in the elution buffer. More preferably the elution is performed with a pH step gradient.

In some embodiments the CEX elution buffer has an alkaline pH, preferably pH 8, most preferably the elution buffer is 20 mM Tris-HCl/pH 8.

In the most preferred embodiments a DEAE Macro-Prep column is directly connected to a Toyoperl SP-650 column, the sample load was performed in sodium acetate buffer pH 4.5 and the elution of G-CSF was performed by a pH step using Tris-HCl buffer pH 8.

In some embodiments of the methods described herein, the solubilising agent and other impurities are removed by the sequential application of the following steps:
  a) AEX,
  b) acid precipitation,
  c) AEX, and
  d) CEX.

In step a), the solubilising agent binds to an anion exchange resin. The resin material may be removed by filtration.

In step b), the pH may be below pH 5, e.g. between 4 and 5. The precipitate may be removed by filtration.

In step c), the residual solubilizing agent binds to the resin. G-CSF remains in the flow through.

In step d) the G-CSF binds to the resin. Residual solubilising agent remains in the flow through.

This may be followed by a step of eluting bound. G-CSF, or functional variant thereof, from the CEX resin by step or gradient elution. The elution buffer may have an increased pH or salt concentration. Increased pH means a ph higher than in step b), i.e. a pH above 5, or above 6, or above 7.

Second Refolding (Completion of Folding)

As already mentioned, it was surprisingly observed that the yields of monomeric, soluble and active G-CSF can be significantly increased when a second cycle of refolding is performed. The experiments suggested that G-CSF obtained using the "classic" sarkosyl/CuSO4 method was not fully refolded.

The second refolding step comprises diluting and then incubating the partially refolded G-CSF.

The preferred solvent for the dilution is a low conductivity buffer or more preferably water. The dilution may be a five-fold, or four-fold, or three-fold or preferably a two-fold dilution. Low conductivity means a conductivity of at least below 2 mS/cm, more preferably below 1 mS/cm. A suitable buffer system is for example Tris/HCl at concentrations of 10 mM Tris or below with a pH value greater than 7. Other buffers with the same low conductivity and pH may also be used.

While not being bound to any theory, the inventors made the following observations. As known in the prior art (Lu 1992) the formation of the second disulfide bridge of G-CSF has a relatively slow kinetic. Not fully refolded intermediates bearing reduced free cysteine moieties are at risk for aggregation and/or precipitation (Rudolph 1990, Rudolph 1996). In the case of G-CSF the intermediate with three unpaired cysteines can exist for a rather long time, depending on the $Cu^{2+}$ concentration and temperatures (Lu 1992). Aggregation and precipitations cause losses of G-CSF during filtration and chromatography steps. The present inventors hypothesized that an improved folding efficacy could result in increased yields in the downstream process. The present inventors found that a second refolding step improved the yield.

The present inventors surprisingly found that incubation during the second refolding step at mildly alkaline pH is beneficial. This is particularly surprising given the fact that G-CSF, especially filgrastim, is a relatively hydrophobic protein, which is less soluble and stable at pH values above its pI (5.65). Best solubility and stability is in acid milieu at pH 4 or below. Therefore, classic purification procedures such as chromatographies are performed at lower pH values, preferably at pH 4-5.5 in acetate buffers. In contrast, the present inventors found that incubation at an alkaline pH further facilitates an increased yield. The present inventors consider the alkaline pH in the absence of an oxidizing agent being important for the complete oxidation of sulfhydryls and thus for forming both natural disulfide bridges of G-CSF.

Thus, the second refolding step may be performed at alkaline pH, i.e. at a pH of 7 or higher. The pH may be above 7. The second, refolding step may be performed at a pH of between 7 and 10, or between 7 and 9, or between 7 and 8.5, or between 7 and 8, or between 7.5 and 10, or between 7.5 and 9, or between 7.5 and 8.5, or at a pH of about 8 or at a pH of 8.

The incubation of the second refolding step is performed in the absence of solubilising agents.

In preferred embodiments:

The second refolding step may be performed, for example, in one of the following buffers: Phosphate, carbonate, borate, Tris, HEPES, MOPS, HEPPS, EPPS, CAPS, CAPSO, CHES, TES, BPS, TAPS, Ethanolamine, Diethanolamine, Triethanolamine, Tricine, Bicine, Acetamidoglycine, Glycinamide or other biocompatible buffer substances having a pKa above 7. A preferred buffer for the second refolding step is Tris-HCl/pH 8, preferentially 10 mM Tris-HCl/pH 8.

The second refolding step may be performed, for example, at a low concentration of residual detergent, such as 0.01 mg/ml or below.

The second refolding step may be performed, for example, at an ionic strength in the solution of 0.02 mol/l or below.

The second refolding step may be performed, for example, at a temperature range of 0°-20° C., or 2°-8° C., or 2°-5° C.

The second refolding step may be performed, for example, for an incubation period of at least 24 h, or more than 24 h, or 30-48 h, or 32-42 h.

The second refolding step may be performed at a low conductivity in the solution, such as 0.1-2 mS/cm, or 0.2-1.5 mS/cm, or 0.5-1.0 mS/cm.

The second refolding step may be performed under cooling.

The second refolding step may be performed under continuous stirring.

One or more of these parameters may be used in the methods described herein.

In some embodiments partially purified G-CSF is used for completion of refolding, preferentially with a purity of about 80-90%.

Preferably the refolding is completed by an incubation of the partially refolded G-CSF in a low conductivity buffer under cooled conditions for more than 12 hours.

Preferably the completion of refolding is performed at conductivity below 2 mS/cm; most preferably the conductivity is below 1 mS/cm.

In some embodiments the completion of refolding is performed at a pH value above 7, preferably at (about) pH 8.

The buffer for the second folding incubation may be 10 mM Tris-HCl, preferably at (about) pH 8.

In some embodiments the incubation for the second folding is performed under cooled conditions, preferentially at 2-8° C.

In preferred embodiments the incubation time of the $2^{nd}$ folding is more than 12 hours, more preferably more than 24 hours, most preferably 32-42 hours.

Particularly preferred conditions for the completion of folding ($2^{nd}$ refolding), based on various optimisation experiments, are those shown in Table I under the column "$2^{nd}$ Refolding".

Final Purification (Polishing Step(S))

The above described combination of a first and a second refolding step results in increased yields of active monomeric G-CSF.

Optionally, and depending on the intended use of the obtained G-CSF, subsequent downstream processes may be performed, such as one or more polishing step(s). The methods described herein may further comprise one or more polishing step(s). The polishing step(s) result(s) in further purification of the refolded G-CSF after the second refolding step.

The subsequent downstream processes (polishing) may comprise the use of AEX and CEX chromatographies, or other methods used in the art for G-CSF polishing/purification, such as, HIC, IMAC, SEC or RP-HPLC (see references of Background section). The polishing step(s) may also comprise combinations of two or more of these methods.

After the second folding step the purity of G-CSF is typically 80-90% (Table III). This does not comply with a pharmaceutical quality. If the product is to be used as an active pharmaceutical ingredient, at least one further polishing step is performed to achieve the desired purity. Such a polishing step removes residual contaminants resulting from the host or from the process. In addition, any product-related substances and related impurities are removed.

AEX

The downstream polishing may comprise one or more AEX step(s). The polishing step may comprise AEX.

The skilled person can select a suitable AEX. The selection of the resin can be made on the basis of the desired separation performance, process times, cleaning robustness, reproducibility, binding capacity, lot-to-lot consistency, and overall economy, etc.

In preferred embodiments, the functional group DEAE is used. The skilled person will appreciate that besides the functional group the nature of the backbone of the AEX resin as well as the size of the beads needs to be considered. In particularly preferred embodiments, a matrix based on methacrylate derivatives (e.g. Macro-Prep® and Toyopearl®) is used. Such a matrix showed particularly good resolution and reproducibility. The methacrylate materials are more rigid and have better life time cycles than for example the frequently used cross linked agarose matrixes (e.g. Sepharose®). As AEX can now be used in a binding mode (in contrast to the previous step for removal of solubilising agents), selective elution conditions, either provided by increasing the salt concentration by steps or gradients, or by decreasing the pH in the elution buffer by steps or gradients, can be used.

AEX resin materials have been discussed above.

The skilled person can choose the appropriate downstream polishing methods, depending on the previously used conditions, such as the buffer, etc. For example, in preferred embodiments, the second refolding step is performed in low conductivity buffer at about pH 8. This is an ideal initial situation for an AEX polishing step in the binding mode and would allow further removal of contaminants and an easy buffer exchange to a low pH buffer, if desired, wherein G-CSF is more soluble and more stable.

CEX

The downstream polishing may comprise one or more CEX polishing step(s). The polishing step may comprise CEX.

As an alternative (or in addition) to an AEX step, a CEX chromatography may also be used as an efficient polishing step. For this method a pH adaption to pH below 5.5 prior to sample load is required to allow a chromatography in the binding mode, which is important for a sufficient protein separation. The functional cation exchange group and the matrix can be selected according to the same criteria as mentioned for AEX. In preferred embodiments, SP and CM functional groups on mothacrylate backbones (Toyopearl®, Macro-Prep®) are used. In particularly preferred embodiments, Toyopearl CM-650 is used, more preferably Toyopearl SP-650 is used.

CEX resin materials have been mentioned above.

Once bound to the CEX resin G-CSF can be eluted with selective conditions, either provided by increasing the salt concentration by steps or gradients, or by increasing the pH in the elution buffer by steps or gradients.

The skilled person knows how optimise the resolution of a chromatography.

In some embodiments, one chromatographic step, AEX or CEX, is sufficient to achieve the desired quality of the G-CSF product.

In other embodiments, the downstream processing comprises two or more polishing steps. For example, the polishing may comprise two or more chromatographic steps. Thus, if desired or necessary, two or more ion exchange polishing steps can be performed. When using two polishing steps, it is preferred to use AEX followed by CEX. In such a case both steps are performed in the binding mode. One advantage of this order is that G-CSF is obtained at an acidic pH at the end, which e.g. allows long term storage of concentrated G-CSF. The use of two IEX polishing steps was demonstrated to result in particularly high purity (Table IV).

The downstream polishing step(s) result(s) in a purity of G-CSF of at least 90%, 91%, 92%, 93%, 94%, 95%, 96%, 97%, 98%, 98.5%, 99%, or 99.5%.

For the calculation, of purity in accordance of the present invention (see Example 13) HPLC chromatograms were used, which were integrated for the main peak (areas). Any remaining "impurities" are so-called "product-related impurities" which means they are G-CSF molecules with modifications, such as oxidation (different species), deamidation, dimerisation, aggregation, or so far not structurally clarified isomerioations (Table IV). Of course these product-related substances are present in traces only. It is of note that in the finally purified G-CSF preparations the "process-related impurities", such as HCP, DNA, or bacterial endotoxins are detectable at very low ppm levels only or not detectable at all (Table IV). Such purity would be reported elsewhere as apparent homogeneity. The analytical methods for determination of the purity are disclosed in Example 13. FIG. 3 shows an example of a SEC-HPLC chromatogram of a purified G-CSF batch (3B) in comparison with a commercially purchased EU-approved medicinal product used as reference (3A). Traces of aggregates are visible left from the main peak. The peak right from the main peak is caused by the solvent and not an impurity. These chromotagrams underline the sufficient quality of the G-CSF, even for pharmaceutical grade, purified according to the described methods.

In some embodiments of the present invention, the completely refolded G-CSF is further purified comprising one or more ion exchange chromatographies.

Preferably, the ion exchange chromatographies comprise an anion exchange chromatography followed by a cation exchange chromatography.

In some embodiments, partially purified G-CSF having a purity of about 80-90% is further purified to more than 95% purity by using two polishing steps: AEX and CEX.

In some embodiments, the AEX step is followed by the CEX step. Preferably, both steps are performed in the binding mode.

Using the methods described herein, G-CSF can be obtained at pharmaceutical grade quality. Such G-CSF preparations are suitable for therapeutic applications or may be used as intermediates for subsequent conjugations, for instances with polyethylene glycol.

In one aspect the invention provides a process for purification of G-CSF. The process may also be used to remove the solubilising agents between the first and second refolding step discussed herein. Provided herein is a process for purification of G-CSF and/or removal of a solubilising agent used for solubilisation of G-CSF from inclusion bodies, the process comprising the following steps:

e) anion exchange chromatography conducted under conditions where G-CSF binds to the resin; and
f) elution of bound G-CSF by step or gradient elution using an elution buffer with decreased pH or increased salt concentration; and,
g) cation exchange chromatography conducted under conditions where G-CSF binds to the resin; and
h) elution of bound G-CSF by step or gradient elution using an elution buffer with increased pH or salt concentration.

"Decreased/increased pH" or "increased salt concentration" refers to the buffer used for elution compared to the buffer for column equilibration, sample loading or washing.

With regard to AEX and CEX, suitable materials and conditions have been discussed above. In preferred embodiments, the process is characterised in that the backbone polymers of the anion and cation exchange resins both comprise methacrylate derivatives.

In some embodiments the functional groups of the AEX resin are diethylaminoethyl (DEAE) groups.

In some embodiments the functional groups of the CEX resin are carboxymethyl (CM) groups.

In some embodiments the backbone polymers of the anion and cation exchange resins do not comprise cross-linked agarose, such as for example Sepharose®.

In preferred embodiments the backbone polymers of the AEX and/or CEX anion and/or cation exchange resins comprise methacrylate derivatives.

In more preferred embodiments the AEX resin is DEAE Macro-Prep (BioRad) and the CEX resin is Toyopearl CM-650 (Tosoh).

In some embodiments the AEX column is equilibrated with low conductivity buffer at pH above 7, preferably with 10 mM Tris-HCl/pH 8.

In some embodiments the G-CSF is eluted from the AEX column by increasing the salt concentration, preferably with a gradient, most preferably with a linear gradient. Preferably the elution is performed with a linear NaCl gradient in Tris-HCl/pH 8 buffer.

In some embodiments, prior to the CEX step, the pH value of the eluted G-CSF from the AEX column is adjusted, preferably the pH is adjusted to a pH below 5.5, most preferably to (about) pH 4.5.

Preferentially the eluted G-CSF from the AEX column is diluted 2-fold with water and the pH is adjusted to (about) 4.5 by titration with 50% acetic acid.

In some embodiments the CEX column is equilibrated with a low conductivity buffer of pH below 5.5, preferably with 20 mM sodium acetate/pH 5.3.

In some embodiments the G-CSF was eluted from the CEX column with increasing salt, preferably with a gradient, most preferably with a linear gradient.

Preferentially the elution of G-CSF from the CEX column is performed with a linear sodium acetate gradient at pH 5.3.

In preferred embodiments the G-CSF is solubilised from IBs, refolded and purified according the order of steps disclosed in the purification scheme of FIG. 2.

In some embodiments of the invention the finally purified G-CSF after polishing is formulated by gel chromatography, preferably using Sephadex G-25.

In some embodiments the formulation buffer contains sorbitol and nolysorbate; more preferably the formulation buffer comprises 10 mM sodium acetate/pH 4/5% (w/v) sorbitol/0.006% (w/v) polysorbate 80.

BRIEF DESCRIPTION OF THE FIGURES

FIG. 1 depicts the two-step refolding strategy, which optional downstream polishing steps for production of biologically active G-CSF. Further details are disclosed in the examples.

FIG. 2 discloses a preferred embodiment, i.e. a sequence of steps starting from G-CSF-containing inclusion bodies and leading to fully refolded and purified G-CSF. Further details are disclosed in the examples.

BRIEF DESCRIPTION OF THE TABLES

Figure 3A:
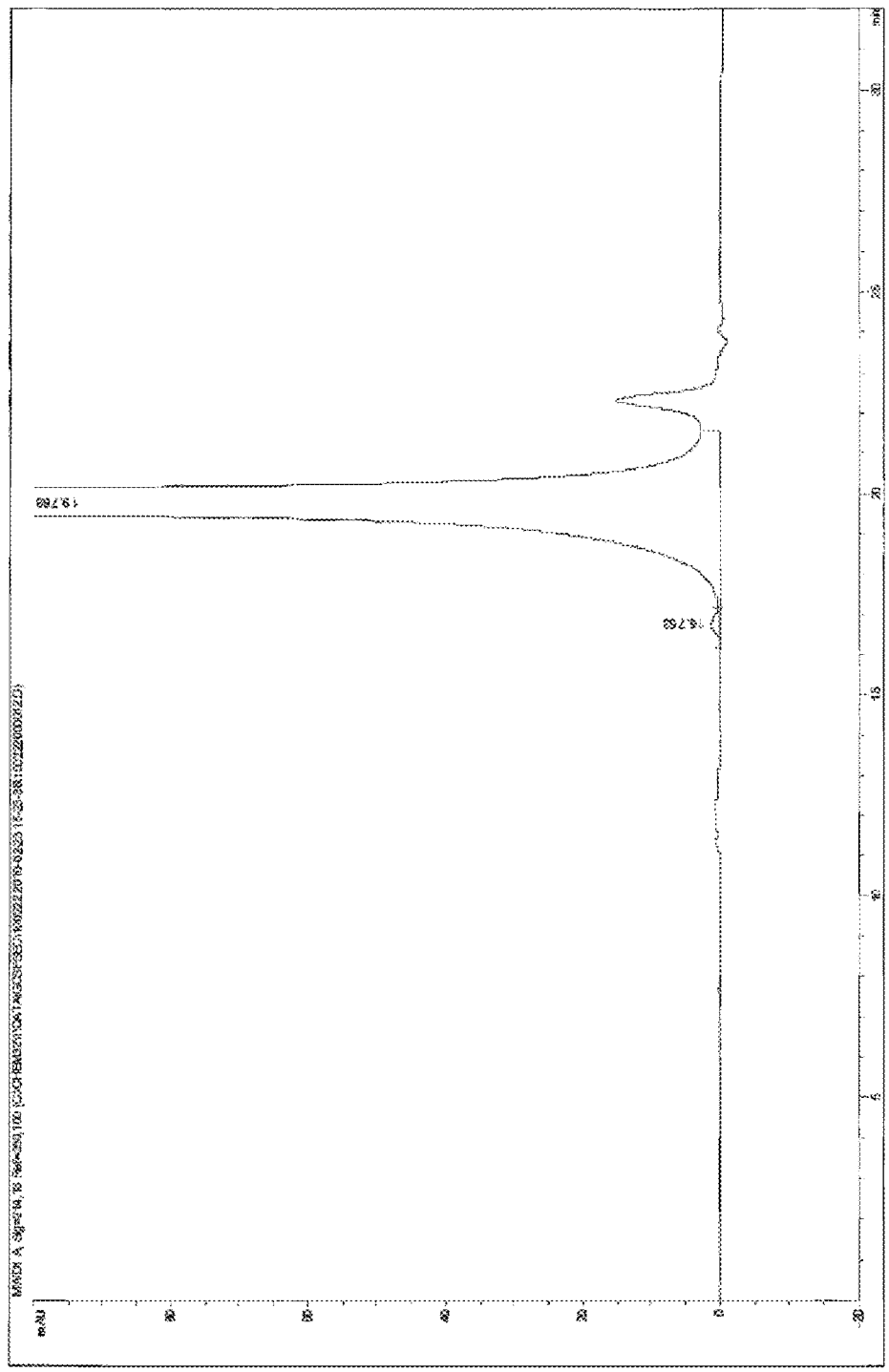
FIGS. 3A and 3B compare SEC-HPLC chromatograms from a purity analysis of a commercially available filgrastim drug product (FIG. 3A) used as reference and the product purified according the sequence summarised in FIG. 2 (FIG. 3B). Further details of the methods are described in details in the examples.

Table I lists preferred conditions for the two refolding steps. The concentrations in the $1^{st}$ refolding incubation result from two-fold dilution of the solubilised G-CSF with water. The $2^{nd}$ refolding incubation is devoid of the reagents sarkosyl and CuSO4 from the first refolding. Further details are mentioned in the examples.

Table II shows the purity and yields of three production runs starting with 650 g washed and frozen, inclusion bodies. The calculation of yields refers to the moist mass of the inclusion bodies. The final purity is calculated from the main peak area in RP-HPLC excluding product-related substances (G-CSF isomers) and product-related impurities. Further details are mentioned in the examples.

Table III shows the values of total purity and of two selected process-related impurities (sarkosyl, endotoxins) during the purification of G-CSF. The ranges indicate the results of the analysis of three G-CSF production lots using different analytical methods. Further details are mentioned in the examples.

Table IV shows the analytical results of different methods on specific impurities and the biological activity of three subsequent G-CSF production lots. The data are taken form routine batch release testing. Further details are mentioned in the examples.

EXAMPLES

Example 1

Fermentation and Expression

The G-CSF (filgrastim) was produced with the recombinant *E. coli* C2523 T7 pol pRG/GCSFa clone (*E. coli* transformed with an expression vector comprising G-CSF). Under aseptic conditions the prepared seed culture media was inoculated with 0.10-0.15 cm$^3$ cell suspensions obtained from a thawed working cell bank vial that was stored in liquid nitrogen. The inoculated seed culture flasks were incubated in a gyratory shaker incubator at 37° C. at 185 rpm. for 24-28 hours. When the mean value of the optical density at 600 nm (OD) of the six shaked flask culture reached 0.9-1.1, the content of the flask was collected into a sterile 5 dm$^3$ glass flask equipped with a silicone tube. The collected 3 dm$^3$ volume seed culture was transferred with a WM323U/R pump to the 100 dm$^3$ fermenter filled up to 75 dm$^3$ with sterile and supplemented production medium (GBA, synthetic medium with glycerol as carbon source). The cultivation was performed under strict aerobic conditions in a submerged culture at 37° C. When the carbon source became exhausted from the medium, a glycerol feeding solution was added to the culture in appropriate rates. The dissolved oxygen tension was maintained at a level not less than 30% during the whole culture period. When the OD value of the culture reached 30, the temperature was decreased to 32° C. and 0.33 mM IPTG was added to induce the expression of G-CSF. The bacteria were further cultivated for producing G-CSF for 5 hours until an OD of 80-95

Example 2

Harvest of Bacteria

Agitation, aeration and feeding of carbon sources were stopped, the culture was cooled below 15° C., and the bacteria were harvested by separation at 11000 g. The cells sedimented in the rotor and were washed out (discharged) by water. The bacterial cell concentrate was collected, diluted back to its half volume with water, and 0.5M NaH$_2$PO$_4$ was added to a final concentration of 10 mM. The total mass of the wet bacterial cells (biomass) were about 10-11.5 kg.

Example 3

Lysis of Bacteria and Inclusion Bodies Preparation

The separated and washed bacteria were disrupted under pressure (100 MPa) by passing through a homogeniser three times. Inclusion bodies wore separated from cell debris by sedimentation in separator at 11000 g. The sedimented inclusion bodies were discharged in washing buffer containing 5 mM DTT, 10 mM NaH$_2$PO$_4$, 5 mM EDTA, and 2% Tween 20 at pH 7.2. The concentrated IB suspension was diluted 2-fold with the same buffer and sedimented again. This washing procedure was repeated two times using 10 mM NaH2PO4 buffer, at the end of the second procedure without dilution. The final sediment of IBs was stored frozen at −80° C.

Example 4

Solubilisaton of Inclusion Bodies

The frozen inclusion bodies (650 g moist mass) were thawed, and dissolved in solubilisation buffer containing 40 mM Tris-HCl, pH 8 and 1% (w/v) N-lauroylsarcosin (sarkosyl) in a total volume of 32.5 dm$^3$. The suspension was incubated at room temperature under continuous stirring.

Example 5

Oxidative Refolding (1$^{st}$ Refolding)

The solubilised IB suspension was diluted 2-fold with water to 0.5% sarkosyl and 20 mM Tris-HCl as final concentrations in a total volume of 65 dm$^3$. CuSO$_4$ was added to a final concentration of 40 µM. G-CSF was oxidized and partially refolded during continuous stirring and airflow in the head space at room temperature for at least 20 hours. The oxidation was terminated by the addition of EDTA at a final concentration of 1 mM.

Example 6

Sarcosyl Removal by AEX Batch Adsorption

Sarkosyl was adsorbed to an anion exchange (AEX) resin in a batch mode. An amount of 20 g AG 1-X8 resin (BioRad, USA) per gram sarkosyl was applied and added to the solution. The suspension was stirred for two hours to bind most of the sarkosyl. The resin was removed by filtration through a 100 µm pore size nylon bag filter mesh. The remaining sarkosyl in the filtrate was completely removed from the product with the subsequent purification steps (Examples 7 and 8).

Example 7

Precipitation of Contaminants at Acid pH

By acidic precipitation at pH 4.3-4.5 some impurities were easily removed while G-CSF remains soluble. Any potential non-specific and undesired co-precipitation of G-CSF was prevented by addition of 1M urea in final concentration. Urea was provided by a 6M stock solution and slowly added to the filtrate of Example 6 with a rate of 1 dm³/min. Subsequently, the pH was decreased by adding ¹/₂₀ volume of 1M sodium acetate pH 4.8. The pH was further lowered to 4.3-4.5 by titrating with 50% acetic acid. The precipitation was allowed for at least one hour. Then the precipitated material was removed by filtration through a depth filter (Pall K700/KS50 dual layer).

Example 8

Residual Sarkosyl Removal and Buffer Exchange by Series-Connected AEX+CEX Chromatographies Sodium acetate 50 mM/pH 4.5 buffer was used for equilibration of 1) a 4 dm³ column packed with DEAE Macro-Prep (Bio-Rad, USA) AEX resin, and 2) an 8 dm³ column packed with Toyopearl SP-650C (Tosoh, Japan) CEX resin. Both columns were connected directly on an ÄKTA process chromatography system (GE Healthcare, Sweden) in a tandem arrangement. After clearance through a 0.2 µm sterile filter, the filtrate of Example 7 was loaded onto the first column. Residual sarkosyl bound to the DEAE resin, while G-CSF remained unbound (non-binding mode) and appeared in the flow-through of the first column. This flow through was loaded directly onto the second column (SP resin), which bound G-CSF (binding mode). A simple step elution with 20 mM Tris-HCl/pH 8 desorbed the G-CSF from the resin. Besides the removal of residual sarkosyl, a buffer exchange from Na-Acetate/pH 4.5 to Tris-HCl/pH 8 was also achieved by this method.

Example 9

2$^{nd}$ Refolding (Completion of Folding)

At this stage the folding of about half of the protein fraction was completed, while the remaining protein was incompletely folded or misfolded. The G-CSF solution eluted from Toyopearl SP-6500 in 20 mM Tris-HCl, pH 8 and was passed through a 0.2 µm sterile filter into a stainless steel vessel. The filtered solution was diluted 2-fold with water. The second incubation for protein folding (2$^{nd}$ Refolding) was carried in a low conductivity environment (<1 mS/cm) at pH 8 under cooling at 2-8° C. for 32-42 hours.

Example 10

Purification by AEX Chromatography (Polishing Step 1)

A column was packed with DEAE Macro-Prep (Bio-Rad, USA) and was equilibrated with 10 mM Tris-HCl/pH8. The solution which resulted from the 2$^{nd}$ refolding (Example 9) was loaded to the DEAE column. The correctly folded G-CSF was eluted by an increasing linear NaCl gradient from 0 mM to 200 mM in 10 mM Tris-HCl/pH 8. The eluted G-CSF was pooled and diluted 2-fold with water. The pH was adjusted to 4.5 by titration with 50% acetic acid.

Example 11

Purification by CEX Chromatography (Polishing Step 2)

For the final polishing step the G-CSF pool collected from the AEX chromatography (Example 10) consisting of correctly folded protein was directly applied onto a CEX column packed with Toyopearl CM-650S resin. The column was equilibrated by 20 mM sodium acetate, pH 5.3. The bound G-CSF was eluted by an increasing linear salt gradient from 20 mM to 400 mM sodium acetate within 24 column volumes at pH 5.3. Fractions with pure G-CSF were collected and pooled for formulation.

Example 12

Formulation of Purified G-CSF by Gel Chromatography

The purified G-CSF as eluted from the CEX column (Example 11) was filtered through a 0.2 µm sterile filter and passed through a 14 dm³ column packed with Sephadex G-25 fine resin equilibrated with formulation buffer (10 mM sodium acetate, pH 4, 5% sorbitol, and 0.006% polysorbate 80). The same buffer was used as running buffer. G-CSF eluted in the void volume in formulation buffer. For a whole batch (35-48 g G-CSF) three subsequent formulation runs on Sephadex G-25, each with one third of the filtered CEX eluate, were performed. The formulated G-CSF was adjusted to a concentration of 0.9-1.0 mg/ml by dilution with formulation buffer, and finally filtered through a 0.2 µm sterile filter capsule. Formulated G-CSF as sterile solution is very stable and can be stored at 2-8° for many months if not years.

Example 13

Analytical Methods

Well-known standard analytical methods were performed in compliance with the European Pharmacopoeia (Ph. Eur.), which contains a monograph for filgrastim describing specific analytical methods (European Directorate for the Quality of Medicines & Health Care (EDQM) (2010): Filgrastim concentrated solution. European Pharmacopoeia 7.0, 2015-2018). For basic techniques the monograph cross-references to other chapters within the European Pharmacopoeia. These specifically referred chapters, which provide a more detailed description of the techniques, are cited in square brackets in the examples below. The utilised reference standards were either commercially purchased authorised drug products (filgrastim), approved by the European Union for medicinal use, or in-house standards which were calibrated using these commercial references. For the analysis of the relative potency in terms of International Units (IU) the international G-CSF Standard of the World Health Organisation (WHO) was used additionally. The test methods used for analysing the purity, the specific impurities, the G-CSF-related proteins and the biological activity (potency) were applied according the Ph. Eur. Monograph with few modifications only. Therefore, in the following, these standard analytical methods, which are known in the art, are described only briefly.

Example 13.1

Polyacrylamide gel electrophoresis (SDS-PAGE): [Ph. Eur. 7, 2.2.31]. SDS-PAGE was used to determine the molecular size, the identity of G-CSF and the purity. The gels had 12% PA and include sodium dodecylsulfate (SDS). The method was used under reducing and non-reducing conditions. Gels were stained with Sypro ruby. To calculate the relative molecular masses (Mr) a panel of marker proteins with defined masses was used.

Example 13.2

Figure 3B:
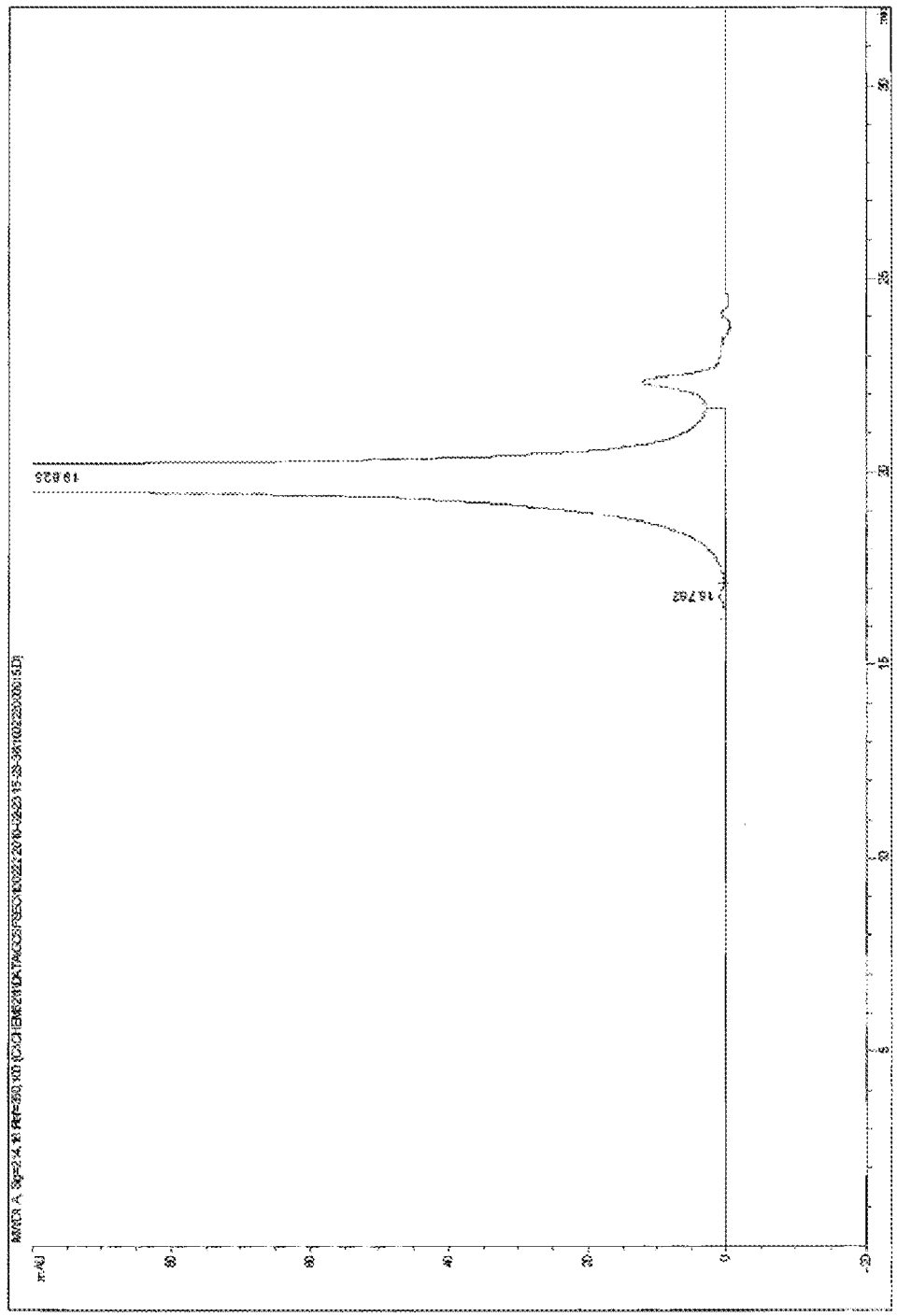

High performance size-exclusion chromatography (SEC-HPLC): [Ph. Eur. 7, 2.2.30]. SEC was used to detect impurities or G-CSF-related substances with molecular masses higher than that of Filgrastim (dimers, aggregates). The detection of the proteins was based on UV absorption. The purity (main peak) and the impurities (dimers, aggregates) were expressed in area % of active substance for each component. The test results were calculated from the average of replicate measurements. FIG. 3 shows an example of a SEC chromatogram of a purified G-CSF batch (3B) in comparison with the reference standard (3A). Traces of aggregates are visible left from the main peak. The peak right from the main peak is caused by the solvent and not an impurity.

Example 13.3

Reversed phase high pressure liquid chromatography (RP-HPLC): [Ph. Eur. 7, 2.2.29]. RP-HPLC was utilised to determine the identity of G-CSF, to calculate the G-CSF content and the purity. The method was also used to identify and quantify product-related substances. The detection of the proteins was based on UV absorption. The related protein impurities were expressed in percentage of active substance area). The test results were calculated from the average of replicate measurements.

Example 13.4

Isoelectric focussing gel electrophoresis (IEF): [Ph. Eur. 7, 2.2.54]. This method was used to detect impurities or product-related substances with charges differing from G-CSF (e.g. deamidated G-CSF). Separation was carried out in polyacrylamide gels containing immobilised pH gradients based on ampholytes. Additionally the isoelectric point (pI) of each protein band was calculated using a set of marker proteins having defined pIs.

Example 13.5

Enzyme-linked immunosorbent assay (ELISA): This method was used for quantitative determination of $E.$ $coli$ host cell protein (HCP) levels. The test was performed by using a commercially purchased (generic) immunoenzymetric assay kit (Cygnus Technologies, no. F410). The solid phase of microtiter strips were coated with affinity-purified polyclonal anti-$E.$ $coli$ antibodies which captured HCP from the test samples. A tracer anti-$E.$ $coli$ antibody labeled with horseradish peroxidase (HRP) simultaneously bound to HCP and the resulting sandwich withstood washing procedures. Bound HCP, respectively HRP, was detected by oxidation of the substrate tetramethylbenzidine (TMB) in presence of hydrogen peroxide. The optical density was measured by an ELISA reader. Quantitation was performed with a calibration graph obtained by measuring HCP calibrators (provided by the kit) in different concentrations. The method was exactly performed according to the instructions of the supplier. HOP concentrations were expressed in ng/ml or ng/mg (ppm).

Example 13.6

Quantitative polymerase chain reaction (qPOR): This assay is used for the determination of $E.$ $coli$ host cell DNA. A commercially available kit was applied designated "res-DNASEQ™ $E.$ $coli$ Residual DNA Quantitation System" which is based on the real-time TaqMan® qPCR technology (Applied Biosystems). The method is very sensitive and specific in detection of DNA contamination. The assay is based on sequence-specific amplification and real-time fluorescence detection of well defined DNA fragments by polymerase chain reaction (PCR) using sequence-specific primers (SSP) and fluorescently labeled hybridization probes (TagMan®). The whole method including instrumentation, reagents, sampling and software-based calculation was performed according to the instructions of the supplier.

Example 13.7

Bacterial endotoxins: [Ph. Eur. 7, 2.6.14, method C]. The detection of gram-negative bacterial endotoxins are globally harmonized standard methods based on amoebocyte lysates from horseshoe crab (*Limulus polyphemus*). This *Limulus* test ("LAL test") was carried out using the turbidimetric kinetic technique (method C) according to the European Pharmacopoeia. The results were expressed in International Units (IU) related to the International Endotoxin Standard BRP.

Example 13.8

Assay for biological activity (relative potency): The biological activity of G-CSF samples was tested in a cell-based in-vitro proliferation assay as described in the filgrastim monograph with the following modifications. The bioassay method was based on the comparison of the change of the cell proliferation of NFS-60 cells, which originated from a murine myeloblastic cell line. NFS-60 cells were treated with dilution series of the test sample and the reference solution in parallel. The proliferation of the NFS-60 cells can be significantly and specifically stimulated with G-CSF. Propagation of the cells was performed in microtest plates for 72 hours. The proliferative effect was detected by using the substrate resazurin (Alamar® Blue) which was converted by viable cells into the fluorescence dye resorufin. The fluorescence signal was detectable with high sensitivity. The parallel line assay calculation of the dose response curves, with at least three points in the linear part of the curves, was used as a statistical evaluation. Acceptance range was between 80% and 125% compared to the reference solution. The relative potency was expressed by International Units (IU) which were defined by internal standards calibrated to the International WHO standard for filgrastim. Fully active, pure human G-CSF possesses a specific biological activity of $1.0 \times 10^8$ IU/mg.

Example 13-9

Peptide mapping: [Ph. Eur. 7, 2.2.55]. The peptide mapping followed by mass spectroscopy (MS) analysis was used for analysis of the disulfide-bridges. The enzymatic cleavage of the peptide bonds procedure was developed on the basic of the Ph. Eur. monograph for filgrastim. The protease used for cleavage was Glutamyl Endopeptidase (EndoGlu-C). Incubation was carried out at 37° C. for 24 hours and stopped by addition of 8M GuHCl and boiling. The peptide mapping procedure was performed under reduced and non-reduced conditions. The resulting differences in the MS spectrum of the peptide profiles for reduced and non-reduced conditions prove the position of the disulfide bonds. Completely folded intact G-CSF (filgrastim) has two disulfide bridges at positions Cys37-Cys43 and Cys65-Cys75, while one cysteine residue is free at position 18.

Alternatively peptides obtained from G-CSF samples after the proteolytic digestion are separated in a RP-HPLC system and detected in UV. This method provides comparative data, as the fingerprint-like chromatogram obtained with the test solution is compared to the chromatogram obtained with the reference material.

LIST OF REFERENCES

1. R. R. Burgess, 1996 "Purification of over produced *E. coli* RNA polymerase σ factors by solubilizing inclusion bodies and refolding from sarkosyl". Methods Enzymol. 273, 145-149
2. David C. Dale, 2002 "Colony-Stimulating Factors for the Management of Neutropenia in Cancer Patients", Aids International Limited Drugs 2002; 62 Suppl. 1, 1-15
3. P. F. Devlin, 1988 "Alteration of amino-terminal codons of human granulocyte-colony-stimulating factor increases expression levels and allows processing by methionine aminopeptidase in *Escherichia coli*", Elsevier Science Publishers B.V. (Biomedical Division) Gene, 65, 13-22
4. Arndt Dietrich et al., January 2003, "Industrial Protein Folding", www.gitverlag.com/go/bioint BIOforum Europe, 1-3
5. European Pharmacopoeia, July 2010 "Filgrastim concentrated solution"; 2015-2018
6. Elanders Östervala, April 2007 "Purification and renaturation of recombinant proteins produced in *Escherichia coli* as inclusion bodies, www.golifesciences.com/protein-purifactoin Application note 18-1112-33 AC, 1-4
7. M. Heidari et al., May 2001 "Expression, purification, and in vitro biological activities of recombinant bovine granulocyte-colony stimulating factor", www.elsevier.com/locate/vetimm Veterinary Immunology and Immunopathology 81, 45-57
8. Holloway C. J. 1994, "Applications of Recombinant DNA Technology in the Production of Glycosylated Recombinant Human Granulocyte Colony Stimulating Factor", European Journal of Cancer Vol. 30 A, Suppl. 3, 82-56
9. Soo-Hyung Kang at al., July 1995, "High Level Expression and Simple Purification of Recombinant Human Granulocyte Colony-Stimulating Factor in *E. coli*, Biotechnology Letters Volume 17 No. 7 687-692
10. Khalilzadeh R., et al., July 2008, "Process development for production of human granulocyte-colony stimulating factor by high cell density cultivation of recombinant *Escherichia coli*, *J. Ind Microbial Biotechnol,* 1643-1650
11. Fiona A. O. Marston, 1986, "The purification of eukaryotic polypeptides synthesized in *Escherichia coli*, Biochem. J. (1986) Vol. 240, 1-12
12. G. Molineux, 2004, "The Design and Development of Pegfilgrastim", Current Pharmaceutical Design., 2004, 10, 1235-1244
13. Dasari Venkata Krishna Rao et al., 2008, "A purification method for improving the process yield and quality of recombinant human granulocyte colony-stimulating factor expressed in *Escherichia coli* and ist characterization, Biotechnol. Appl. Biochem. (2008) 50, 77-87
14. Harald Tschesche, 1990, "Modern Methods in Protein- and Nucleic Acid Research", Walter de Gruyter, Berlin, N.Y., 149-171
15. Rainer Rudolph et al., January 1996, "In vitro folding on inclusion body proteins", The FASEB Journal Vol. 10, 49-56
16. Ana L S Vanz et al., April 2008, "Human granulocyte colony stimulating factor 8hG-CSF): cloning, overexpression, purification and characterization", Microbial Cell Factories 2008, www.micorbialcellfactories.com/content/7/1/13, 1-12
17. Chao Zhan WANG et al., 2005, "Refolding with Simultaneous Purification of Recombinant Human Granulocyte Colony-stimulating Factor from *Escherichia coli*, Chinese Chemical Letters Vol. 16 No. 3 www.imm.ac.cn/journal/ccl.html, 389-392
18. Karl Welte et al., September 1996, "blood", Blood Vol. 88 No. 8, American Society of Hematology, www.bloodjournal.org, 1907-1929
19. Paul WINGFIELD et al., 1988, "Characterization of recombinant-derived granulocyte-colony stimulating factor (G-CSF)", Biochem. J. Vol. 256, 213-218
20. Krisztina M. Zsebo et al., 1986, "Recombinant Human Granulocyte Colony Stimulating Factor: Molecular and Biological Characterization, Immunobiol., Vol. 173, 175-184
21. Lu et al, 1992, The Journal of biological Chemistry, Vol 267:8770-8777
22. WO 03/051922 A1
23. WO 01/87925 A2
24. WO 01/04154 A1
25. WO 00/02901
26. U.S. Pat. No. 6,489,450 B2
27. U.S. Pat. No. 5,849,883
28. U.S. Pat. No. 5,681,720
29. U.S. Pat. No. 5,055,555
30. EP 1 837 346 A2
31. EP 1 630 173 A2
32. EP 0 219 874 A2
33. WO 2010/146599 A1
34. WO 2008/096370 A3
35. WO 2006/135176 A1
36. WO 2006/097944 A2
37. WO 2004/015124 A1
38. WO 2004/001056 A1
WO 98/53072
40. WO 89/10932
41. WO 87/01132

The invention claimed is:

1. A method for refolding granulocyte colony stimulating factor (G-CSF) from inclusion bodies, comprising:
   a) solubilising G-CSF in the presence of a solubilising agent selected from the group consisting of a detergent, a tenside and a surfactant;
   b) performing an oxidation and first refolding step, comprising incubating the solubilised G-CSF in the presence of an oxidizing agent and the solubilising agent;
   c) removing the solubilising agent by ion exchange resin adsorption and/or ion exchange chromatography, and optionally performing an acid precipitation; and
   d) performing a second refolding step at a pH value above pH 7, comprising diluting the G-CSF of step (c) with a low conductivity buffer or water and incubating the diluted G-CSF at a conductivity below 2 mS/cm for more than 12 hours, wherein the solubilizing agent after step c) is below 0.01 mg/ml.

2. The method according to claim 1, wherein the inclusion bodies are from a microorganism, preferably from *E. coli*.

3. The method according to claim 1, wherein the G-CSF is recombinant bovine or human methionyl-G-CSF.

4. The method according to claim 1, wherein the solubilising agent is N-Lauroylsarcosine.

5. The method according to claim 1, wherein the oxidizing agent is $CuSO_4$.

6. The method according to claim 1, wherein the solubilisation of G-CSF is performed at a pH value greater than pH 7.

7. The method according to claim 1, wherein the solubilising agent is N-Lauroylsarcosine at a concentration of 0.5% to 1.5%.

8. The method according to claim 1, wherein the oxidation and first refolding step is performed for at least two hours.

9. The method according to claim 1, wherein the oxidation and first refolding step is performed under airflow and without cooling.

10. The method according to claim 1, wherein the oxidation and first refolding step is performed at a pH value of 7-9 and/or at a temperature of 20-28° C. and/or for 15-25 hours.

11. The method according to claim 1, wherein the removal of the solubilising agent in step (c) comprises: anion exchange chromatography (AEX) and cation exchange chromatography (CEX), optionally in this order.

12. The method according to claim 1 wherein the removal of the solubilising agent in step (c) comprises:
   a) binding to an anion exchange resin material by mixing the G-CSF solution with the suspended resin material and removal of the resin material by filtration, and/or
   b) ion exchange chromatography under conditions where the solubilising agent binds to the resin and G-CSF remains in the flow through and/or,
   c) ion exchange chromatography under conditions where G-CSF binds to the resin and the solubilising agent remains in the flow through.

13. The method according to claim 1 wherein the solubilising agent and other impurities are removed by the sequential application of the following steps:
   (i) anion exchange chromatography (AEX),
   (ii) acid precipitation,
   (iii) anion exchange chromatography (AEX), and
   (iv) cation exchange chromatography (CEX).

14. The method according to claim 1 wherein the solubilising agent and other impurities are removed by the sequential application of the following steps:

a) binding of the solubilising agent to an anion exchange resin material by mixing the G-CSF solution with the suspended resin material and removal of the resin material by filtration;
b) precipitation of impurities by lowering the pH below pH 5 and by removal of the precipitate by filtration;
c) anion exchange chromatography conducted under conditions wherein the residual solubilising agent binds to the resin and G-CSF remains in the flow through;
d) cation exchange chromatography conducted under conditions wherein G-CSF binds to the resin and the residual solubilising agent remains in the flow through; and
e) elution of bound G-CSF from the cation exchange resin by step or gradient elution using an elution buffer with increased pH or salt concentration.

15. The method according to claim 1, wherein the second refolding step is performed under cooled conditions.

16. The method according to claim 1, wherein the second refolding step is performed at a temperature of 2-8° C. and/or for at least 24 hours.

17. The method according to claim 1, wherein the method further comprises a polishing step, which comprises one or more ion exchange chromatographies.

18. The method according to claim 17, wherein the one or more ion exchange chromatographies in the polishing step comprise(s) an anion exchange chromatography followed by a cation exchange chromatography.

19. The method of claim 17, wherein the one or more ion exchange chromatographies comprise(s) the following steps:
a) anion exchange chromatography conducted under conditions where G-CSF binds to the resin;
b) elution of bound G-CSF by step or gradient elution using an elution buffer with decreased pH or increased salt concentration;
c) cation exchange chromatography conducted under conditions where G-CSF binds to the resin;
d) elution of bound G-CSF by step or gradient elution using an elution buffer with increased pH or salt concentration;

characterised in that the backbone polymers of the anion and cation exchange resins both comprise methacrylate derivatives.

* * * * *

UNITED STATES PATENT AND TRADEMARK OFFICE
CERTIFICATE OF CORRECTION

PATENT NO. : 9,458,207 B2  
APPLICATION NO. : 14/386128  
DATED : October 4, 2016  
INVENTOR(S) : Ferenc Felföldi et al.

It is certified that error appears in the above-identified patent and that said Letters Patent is hereby corrected as shown below:

In the Specification

At Column 8, Line 28, "nigh" should be "high"

At Column 8, Line 52, "polyoeptides" should be "polypeptides"

At Column 10, Line 58, "C-CSF" should be "G-CSF"

At Column 11, Line 59, "tensile" should be "tenside"

At Column 12, Line 4, there should be no "," after the word "increased"

At Column 14, Line 57, "RNA polymerase factors" should be "RNA polymerase σ factors"

At Column 15, Line 58, there should be no "." after the word "bound"

At Column 16, Line 35, there should be no "." after "AG"

At Column 17, Line 3, there should be no "," after the word "resin"

At Column 17, Line 14, "filgrastin" should be "filgrastim"

At Column 21, Line 31, "(Polishing Step(S))" should be "(Polishing Step(s))"

At Column 22, Line 44, "knows how optimise" should be "knows how to optimise"

At Column 23, Line 4, "isomerioations" should be "isomerisations"

At Column 23, Line 29, "80-901" should be "80-90%"

Signed and Sealed this  
Third Day of April, 2018

Andrei Iancu  
*Director of the United States Patent and Trademark Office*

CERTIFICATE OF CORRECTION (continued)
U.S. Pat. No. 9,458,207 B2

At Column 24, Line 41, "nolysorbate" should be "polysorbate"

At Column 25, Line 4, there should be no "," after the word "frozen"

At Column 25, Line 56, a --.-- should be inserted after "80-95"

At Column 26, Line 10, "wore separated" should be "were separated"

At Column 29, Line 61, "HOP" should be "HCP"

At Column 29, Line 66, "qPOR" should be "qPCR"

At Column 30, Line 53, the heading "Example 13-9" should be "Example 13.9"

At Column 32, Line 53, "WO 98/53072" should be "39. WO 98/53072"